US012186328B2

(12) United States Patent
Savage et al.

(10) Patent No.: US 12,186,328 B2
(45) Date of Patent: Jan. 7, 2025

(54) USE OF CSA COMPOUNDS TO STIMULATE STEM CELLS AND HAIR GROWTH

(71) Applicants: Paul B. Savage, Mapleton, UT (US); Michael C. Moore, Chandler, AZ (US); Chad S. Beus, Spanish Fork, UT (US)

(72) Inventors: Paul B. Savage, Mapleton, UT (US); Michael C. Moore, Chandler, AZ (US); Chad S. Beus, Spanish Fork, UT (US)

(73) Assignee: Brigham Young University, Provo, UT (US)

( * ) Notice: Subject to any disclaimer, the term of this patent is extended or adjusted under 35 U.S.C. 154(b) by 359 days.

(21) Appl. No.: 16/880,590

(22) Filed: May 21, 2020

(65) Prior Publication Data

US 2020/0368253 A1 Nov. 26, 2020

Related U.S. Application Data

(60) Provisional application No. 62/852,110, filed on May 23, 2019.

(51) Int. Cl.
*A61K 31/575* (2006.01)
*A61K 9/00* (2006.01)

(52) U.S. Cl.
CPC .......... *A61K 31/575* (2013.01); *A61K 9/0014* (2013.01)

(58) Field of Classification Search
CPC .. A61K 31/575; A61K 9/0014; A61K 9/0017; A61P 3/10; A61Q 7/00
See application file for complete search history.

(56) References Cited

U.S. PATENT DOCUMENTS

| | | | |
|---|---|---|---|
| 821,187 | A | 5/1906 | Peters |
| 3,843,779 | A | 10/1974 | Norfleet |
| 4,248,236 | A | 2/1981 | Linder |
| 4,284,236 | A | 8/1981 | Bradshaw |
| 4,289,755 | A | 9/1981 | Dhabhar |
| 4,296,206 | A | 10/1981 | Simons, Jr. |
| 4,473,988 | A | 10/1984 | Scott |
| 4,661,341 | A | 4/1987 | Benedict et al. |
| 4,723,950 | A | 2/1988 | Lee |
| 4,765,855 | A | 8/1988 | Geoffroy-Dechaume et al. |

(Continued)

FOREIGN PATENT DOCUMENTS

| | | |
|---|---|---|
| CA | 2322847 A1 | 9/1999 |
| CA | 2640584 A1 | 8/2007 |

(Continued)

OTHER PUBLICATIONS

Sentamilselvi et. al., Int. J. Trichology, vol. 1(2), pp. 100-108, publ. Jul. 2009 (Year: 2009).*

(Continued)

*Primary Examiner* — Sarah Pihonak
(74) *Attorney, Agent, or Firm* — Workman Nydegger

(57) ABSTRACT

The present disclosure describes compositions and methods for regenerating tissue and/or preventing tissue loss by stimulating stem cells. A method includes providing a treatment composition including one or more CSA compounds and a carrier, applying the treatment composition to a targeted tissue region of a subject, and the treatment composition stimulating tissue regeneration and/or preventing tissue degradation at the targeted region of the subject.

20 Claims, 19 Drawing Sheets

(56) References Cited

U.S. PATENT DOCUMENTS

| | | |
|---|---|---|
| 4,842,593 A | 6/1989 | Jordan et al. |
| 4,865,855 A | 9/1989 | Hansen et al. |
| 4,972,848 A | 11/1990 | Di et al. |
| 5,025,754 A | 6/1991 | Plyler |
| 5,286,479 A | 2/1994 | Garlich et al. |
| 5,310,545 A | 5/1994 | Eisen |
| 5,352,682 A | 10/1994 | Sipos |
| 5,356,630 A | 10/1994 | Laurencin et al. |
| 5,364,650 A | 11/1994 | Guthery |
| 5,380,839 A | 1/1995 | Mccall et al. |
| 5,552,057 A | 9/1996 | Hughes et al. |
| 5,624,704 A | 4/1997 | Darouiche et al. |
| 5,687,714 A | 11/1997 | Kolobow et al. |
| 5,721,359 A | 2/1998 | Dunn et al. |
| 5,763,430 A | 6/1998 | Zasloff |
| 5,919,183 A | 7/1999 | Field |
| 6,117,332 A | 9/2000 | Hatch et al. |
| 6,143,738 A | 11/2000 | Zasloff |
| 6,217,896 B1 | 4/2001 | Benjamin |
| 6,224,622 B1 | 5/2001 | Kotzev |
| 6,228,393 B1 | 5/2001 | Dicosmo et al. |
| 6,329,488 B1 | 12/2001 | Terry et al. |
| 6,344,184 B1 | 2/2002 | Rolla |
| 6,350,738 B1 | 2/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,803,030 B2 | 10/2004 | De et al. |
| 6,803,066 B2 | 10/2004 | Traeder et al. |
| 6,824,044 B1 | 11/2004 | Lapstun et al. |
| 6,872,303 B2 | 3/2005 | Knapp et al. |
| 6,872,306 B2 | 3/2005 | Shen |
| 6,939,376 B2 | 9/2005 | Betts et al. |
| 7,226,577 B2 | 6/2007 | Cappelletti et al. |
| 7,235,552 B1 | 6/2007 | Hesse et al. |
| 7,381,439 B2 | 6/2008 | Hilgren et al. |
| 7,481,973 B2 | 1/2009 | Beilfuss et al. |
| 7,611,692 B2 | 11/2009 | Cappelletti et al. |
| 7,659,061 B2 | 2/2010 | Hendl et al. |
| 7,850,947 B2 | 12/2010 | Cappelletti et al. |
| 7,854,941 B2 | 12/2010 | Urban et al. |
| 7,993,903 B2 | 8/2011 | Hayakawa et al. |
| 7,999,390 B2 | 8/2011 | Ishigaki et al. |
| 8,420,050 B2 | 4/2013 | Cappelletti et al. |
| 8,444,954 B2 | 5/2013 | Cappelletti et al. |
| 8,529,681 B1 | 9/2013 | Hibbs et al. |
| 8,530,002 B1 | 9/2013 | Hibbs et al. |
| 8,557,031 B1 | 10/2013 | Hibbs et al. |
| 8,691,252 B2 | 4/2014 | Savage |
| 8,787,857 B2 | 7/2014 | Ezaki |
| 9,180,132 B2 | 11/2015 | Fein et al. |
| 9,434,759 B1 | 9/2016 | Savage |
| 9,527,883 B2 | 12/2016 | Savage et al. |
| 9,533,063 B1 | 1/2017 | Savage |
| 10,226,550 B2 | 3/2019 | Savage et al. |
| 10,441,595 B2 | 10/2019 | Genberg et al. |
| 2002/0019376 A1 | 2/2002 | Savage et al. |
| 2002/0091278 A1 | 7/2002 | Savage et al. |
| 2002/0091433 A1 | 7/2002 | Ding et al. |
| 2002/0115121 A1 | 8/2002 | Garwin |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2003/0232791 A1 | 12/2003 | Levitt et al. |
| 2004/0009227 A1 | 1/2004 | Yao |
| 2004/0011358 A1 | 1/2004 | Smaldone et al. |
| 2004/0018154 A1 | 1/2004 | Pan et al. |
| 2004/0058974 A1 | 3/2004 | Courtney et al. |
| 2004/0071781 A1 | 4/2004 | Chattopadhyay et al. |
| 2004/0126409 A1 | 7/2004 | Willcox et al. |
| 2004/0134292 A1 | 7/2004 | Roth |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0014738 A1 | 1/2006 | Wachendorff-neumann et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0170563 A1 | 7/2007 | Chen |
| 2007/0190066 A1 | 8/2007 | Savage et al. |
| 2007/0190067 A1 | 8/2007 | Savage et al. |
| 2007/0190558 A1 | 8/2007 | Savage et al. |
| 2007/0243225 A1 | 10/2007 | Mckay |
| 2007/0269375 A1 | 11/2007 | Chen et al. |
| 2008/0085949 A1 | 4/2008 | Mcghee |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0024101 A1 | 1/2009 | Toshishige et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0124591 A1 | 5/2009 | Diamond et al. |
| 2009/0226884 A1 | 9/2009 | Tsujimoto et al. |
| 2009/0252781 A1 | 10/2009 | Sawhney et al. |
| 2009/0279944 A1 | 11/2009 | Schmitz et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0033540 A1 | 2/2011 | Daniloff et al. |
| 2011/0071099 A1 | 3/2011 | Bielawska et al. |
| 2011/0091376 A1 | 4/2011 | Savage |
| 2011/0123624 A1 | 5/2011 | Zasloff |
| 2011/0135742 A1 | 6/2011 | Kim et al. |
| 2011/0171144 A1 | 7/2011 | Wang et al. |
| 2011/0230589 A1 | 9/2011 | Maggio et al. |
| 2012/0088733 A1 | 4/2012 | Kim et al. |
| 2012/0128793 A1 | 5/2012 | Miller et al. |
| 2013/0004586 A1 | 1/2013 | Vachon et al. |
| 2013/0022651 A1 | 1/2013 | Savage |
| 2013/0034500 A1 | 2/2013 | Savage et al. |
| 2013/0040265 A1 | 2/2013 | Park et al. |
| 2013/0053507 A1 | 2/2013 | Savage |
| 2013/0089580 A1 | 4/2013 | Boutros |
| 2013/0137668 A1 | 5/2013 | Fein et al. |
| 2013/0234842 A1 | 9/2013 | Leitz |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0243842 A1 | 9/2013 | Genberg et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0062960 A1 | 3/2014 | Kim et al. |
| 2014/0107090 A1 | 4/2014 | Beus et al. |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0315873 A1 | 10/2014 | Beus et al. |
| 2014/0336131 A1 | 11/2014 | Savage et al. |
| 2014/0363780 A1 | 12/2014 | Vazquez et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2015/0140063 A1 | 5/2015 | Savage |
| 2015/0203257 A1 | 7/2015 | Canegallo |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |

(56) References Cited

U.S. PATENT DOCUMENTS

| | | |
|---|---|---|
| 2015/0314342 A1 | 11/2015 | Beus et al. |
| 2015/0366880 A1 | 12/2015 | Genberg et al. |
| 2015/0374719 A1 | 12/2015 | Genberg et al. |
| 2015/0374720 A1 | 12/2015 | Genberg et al. |
| 2016/0022702 A1 | 1/2016 | Savage et al. |
| 2016/0045421 A1 | 2/2016 | Vazquez et al. |
| 2016/0052959 A1 | 2/2016 | Savage |
| 2016/0096864 A1 | 4/2016 | Savage |
| 2016/0193232 A1 | 7/2016 | Beus et al. |
| 2016/0199390 A1 | 7/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Genberg et al. |
| 2017/0258963 A1 | 9/2017 | Savage et al. |
| 2018/0164221 A1 | 6/2018 | Singh et al. |
| 2018/0280550 A1 | 10/2018 | Savage |
| 2019/0076581 A1 | 3/2019 | Savage et al. |

FOREIGN PATENT DOCUMENTS

| | | | | |
|---|---|---|---|---|
| CA | 2842460 | A1 | | 1/2013 |
| CA | 2848567 | A1 | | 3/2013 |
| CA | 2888259 | A1 | | 4/2014 |
| CA | 2741177 | C | | 3/2018 |
| CN | 1236322 | A | | 11/1999 |
| CN | 101247838 | A | | 8/2008 |
| CN | 101378761 | A | | 3/2009 |
| CN | 102145005 | A | | 8/2011 |
| CN | 102172356 | A | | 9/2011 |
| CN | 104039369 | A | | 9/2014 |
| CN | 104080458 | A | | 10/2014 |
| CN | 104080459 | A | | 10/2014 |
| CN | 107670024 | A | * | 2/2018 ......... A61K 38/1875 |
| DE | 1037074 | B | | 8/1958 |
| EP | 0341951 | A2 | | 11/1989 |
| EP | 1208844 | A1 | | 5/2002 |
| EP | 1219631 | A1 | | 7/2002 |
| EP | 0832094 | B1 | | 2/2004 |
| EP | 1058552 | B1 | | 6/2004 |
| EP | 1311531 | B1 | | 5/2016 |
| JP | 60-080457 | A | | 5/1985 |
| JP | 02-014741 | A | | 1/1990 |
| JP | 04-074026 | B2 | | 11/1992 |
| JP | 06-153779 | A | | 6/1994 |
| JP | 07-501826 | A | | 2/1995 |
| JP | 09-248454 | A | | 9/1997 |
| JP | 2002-505292 | A | | 2/2002 |
| JP | 2002-515019 | A | | 5/2002 |
| JP | 2002-255771 | A | | 9/2002 |
| JP | 2002-534532 | A | | 10/2002 |
| JP | 2002-538093 | A | | 11/2002 |
| JP | 2004-506599 | A | | 3/2004 |
| JP | 2004-506645 | A | | 3/2004 |
| JP | 2009-131625 | A | | 6/2009 |
| JP | 2010-059194 | A | | 3/2010 |
| JP | 2010-533051 | A | | 10/2010 |
| JP | 2010-538074 | A | | 12/2010 |
| JP | 2011-527702 | A | | 11/2011 |
| JP | 2014-500741 | A | | 1/2014 |
| JP | 2014-520900 | A | | 8/2014 |
| JP | 2014-530191 | A | | 11/2014 |
| JP | 2014-530192 | A | | 11/2014 |
| JP | 2017-519036 | A | | 7/2017 |
| WO | 95/24415 | A1 | | 9/1995 |
| WO | 98/05337 | A1 | | 2/1998 |
| WO | 98/27106 | A1 | | 6/1998 |
| WO | 99/44616 | A1 | | 9/1999 |
| WO | 99/45024 | A1 | | 9/1999 |
| WO | 00/35375 | A1 | | 6/2000 |
| WO | 00/42058 | A1 | | 7/2000 |
| WO | 02/14342 | A1 | | 2/2002 |
| WO | 02/67979 | A1 | | 9/2002 |
| WO | 03/15757 | A1 | | 2/2003 |
| WO | 03/66119 | | | 8/2003 |
| WO | 03/90799 | A1 | | 11/2003 |
| WO | 2004/082588 | A2 | | 9/2004 |
| WO | 2004/112852 | A1 | | 12/2004 |
| WO | 2007/089903 | A2 | | 8/2007 |
| WO | 2007/089906 | A2 | | 8/2007 |
| WO | 2007/089907 | A2 | | 8/2007 |
| WO | 2007/134176 | A2 | | 11/2007 |
| WO | 2008/038965 | A1 | | 4/2008 |
| WO | 2008/048340 | A2 | | 4/2008 |
| WO | 2008/096149 | A2 | | 8/2008 |
| WO | 2009/049370 | A1 | | 4/2009 |
| WO | 2009/079066 | A2 | | 6/2009 |
| WO | 2009/144708 | A1 | | 12/2009 |
| WO | 2010/006192 | A1 | | 1/2010 |
| WO | 2010/036427 | A1 | | 4/2010 |
| WO | 2010/062562 | A1 | | 6/2010 |
| WO | 2011/066260 | A2 | | 6/2011 |
| WO | 2011/109704 | A1 | | 9/2011 |
| WO | 2012/061651 | A1 | | 5/2012 |
| WO | 2013/013221 | A1 | | 1/2013 |
| WO | 2013/013223 | A1 | | 1/2013 |
| WO | 2013/029055 | A1 | | 2/2013 |
| WO | 2013/029059 | A1 | | 2/2013 |
| WO | WO-2013040265 | A1 | * | 3/2013 ........... A61K 31/575 |
| WO | 2013/109236 | A2 | | 7/2013 |
| WO | 2013/131060 | A1 | | 9/2013 |
| WO | 2013/163359 | A1 | | 10/2013 |
| WO | 2013/167743 | A1 | | 11/2013 |
| WO | 2014/062960 | A1 | | 4/2014 |
| WO | 2014/107740 | A2 | | 7/2014 |
| WO | 2014/151411 | A1 | | 9/2014 |
| WO | 2015/058087 | A1 | | 4/2015 |
| WO | 2015/138716 | A2 | | 9/2015 |
| WO | 2015/200815 | A1 | | 12/2015 |
| WO | 2016/172543 | A1 | | 10/2016 |
| WO | 2016/186821 | A1 | | 11/2016 |
| WO | 2017/053355 | A1 | | 3/2017 |

OTHER PUBLICATIONS

Shi et al., CN 107670024 A, English translation, publ. Feb. 9, 2018 (Year: 2018).*
Bondaryk, M. et al., "Antifungal agents commonly used in the superficial and mucosal candidiasis treatment: mode of action and resistance development", Postep. Derm., Alergol., vol. 30, No. 5, pp. 293-301. 2013.
European Search Report received for EP Patent Application No. 20810836.5, mailed on Jun. 30, 2022, 7 pages.
Martin, L., WebMD, 2012, pp. 1-25.
Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Dumortier G, (A review of poloxamer 407 pharmaceutical and pharmacological characteristics. Pharm Res. Dec. 2006;23(12):2709-28. doi: 10.1007/S11095-006-9104-4. Epub Nov. 11, 2006. PMID: 17096184.).
Lawrence, Toby (The Nuclear Factor NF-? B Pathway in Inflammation, Cold Spring Harb Perspect Biol. Dec. 2009; 1(6): a001651).
Graterol et al., "Ultrastructural changes in premalignant and malignant lesions of the uterine cervix with papillomavirus infection", Journal of Cancer Research and Experimental Oncology, vol. 2, No. 3, Sep. 2010, pp. 35-42.
Hao et al., "A Phase I and Pharmacokinetic Study of Squalamine, an Aminosterol Angiogenesis Inhibitor", Clin Cancer Res, vol. 9, 2003, pp. 2465-2471.
Kwon, Ed., Polymeric Drug Delivery Systems, Taylor & Francis Group, LLC; pp. 1-653, 2005, pp. 350-351.
Lai XZ ( Ceragenins: cholic acid-based mimics of antimicrobial peptides. Acc Chern Res. Oct. 2008;41 (10): 1233-40. doi: 10.1021/ar700270t. Epub Jul. 11, 2008. PMID: 18616297.
McIntosh et al., "Towards Non-Invasive Screening of Skin Lesions by Near-Infrared Spectroscopy", The Journal of Investigative Dermatology, vol. 116, No. 1, 2001, pp. 175-181.

(56) References Cited

OTHER PUBLICATIONS

Schiller et al., "Potentiation of Platinum Antitumor Effects in Human Lung Tumor Xenografts by the Angiogenesis Inhibitor Squalamine: Effects on Tumor Neovascularization", Clin Cancer Res., vol. 5, 1999, pp. 4287-4294.
"Mouth rinse" definition by Medical dictionay. Retrieved from http://medical-dictionary.thefreedictionary.com/mouth-i-rinse, 2015.
"Quaternary Ammoniuim Compounds", Van Nostrand's Scientific Encyclopedia, Jan. 1, 2006, John Wiley & Sons, Inc.
Ahmed, Hydrogel: Preparation, characterization, and applications: A review, Journal of Advanced Research (2015) 6: 105-121 (Year: 2015).
Alhanout K et al: "Squalamine as an example of a new potent antimicrobial agents class: a critical review.", Current Medicinal Chemistry 2010, vol. 17, No. 32, 2010, pp. 3909-3917.
BASF, Pluronic (Registered) Block Copolymer NF Grades (Poloxamer NF Grades), Technical Bulletive (2004).
Berge et al. "Pharmaceutical Salts." Journal of Pharmaceutical Sciences, 66(1): 1977, 1-19.
Bondaryk et al. Postep. Derm. Alergol., 2013, vol. 5, pp. 293-301.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Cipolla et al., "Inhaled antibiotics to treat lung infection", Pharm Pat Anal., Sep. 2013.
csabiotech.com, Uncategorized: CSA Biotechnologies LLC. posted by admin on Apr. 5, 2011 (Year: 2011).
Czernomysy-Furowicz et al. Etiological agents of mastitis in dairy cows on a farm in the West Pomeranian Region. Acta Sci. Pol., Zootechnica 7(1) 2008, 3-10.
De Haas et al. Associations between pathogen-specific cases of clinical mastitis and somatic cell count patterns. J. Dairy Sci. 87: 95-105.
Dean et al.; Flavor Associated with Fish Meal in Diets Fed to Broiler Chickens; 1968; Can. J. Animal Sci .; 49:11-15 (Year: 1968).
Deepak B. Salunke et al., "Amino Functionalized Novel Cholic Acid Derivatives Induce HIV-1 Replication and Syncytia Formation in T Cells", J. Med. Chem. 2006.
Derakhshandeh et al., "Thermosensitive Pluronic hydrogel: prolonged injectable formulation for drug abuse", Drug Design, Development and Therapy, 2010, 255-262.
Ding, et al., "Correlation of the Antibacerial Activities of Cationic Peptid Antibiotics and Cationic Steroid Antibiotics", J. Med. Chem., vo. 45, pp. 663-669 (Year: 2002).
Dumortier, Getal. (Pharmaceutical Research, vol. 23, No. 12, Dec. 2006).
Feng, Theses Brigham Young University, BYU Scholars Archive, dated Dec. 19, 2011, 892.
Ganot (WO 2009/144708 A) (Year: 2009).
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2013/065510, dated Apr. 30, 2015.
International Search Report for PCT Application No. PCT/US2014/034986 dated Aug. 28, 2014.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2009/0475485 dated Feb. 17, 2010.
Sogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Jacob; Feeding Fishmeal to Poultry; https://articles.extension.org/pages/67357/feeding-fishmeal-to-poultry; May 5, 2015; accessed Sep. 10, 2018 (Year: 2015).
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Kaltsas et al., Endocrine-Related Cancer (2005) 12 683-699.
Leszczynska et al. (J Antimicrob Chemother, published Nov. 7, 2012), Bacterial activity of cationic lipids, pp. 1-9).
Louw et al., "Recueil des Travaux Chimiques des Pays-Bas et la Belgique", vol. 73, pp. 667-676, 1954.
No author listed. Novel antibiotic coating shows potential for use on surgical implants. Healio website. Dec. 21, 2005. healio.com/orthopedics/news/online/%7BdcOe6031-1f10-4b3c-abf6-f50b9cfd683f%7D/novel-antibiotic-coating-shows-potential-for-use-on-surgical-implants. Accessed Jun. 2, 2019. (Year: 2005).
Notice of Allowance received for U.S. Appl. No. 14/257,776, mailed on Mar. 25, 2016.
Ogata et al. Intramammary application of ozone therapy to acute clinical mastitis in dairy cows. J. Vet. Med. Sci. 62(7): 681-686, 2000.
Opsenica D, et al., "Cholic Acid Derivatives as 1,2,4,5-Tetraoxane Carriers: Structure and Antimalarial and Antiproliferative Activity", J. Med Chem. Aug. 2000.
Oxford Dictionaries (on-line) definition of Adsorb ([Retrieved from internet <URL: http://www.oxforddictionaries.com/us/definition/american_english/adsorb >] [Downloaded Mar. 10, 2015]).
P. B. Savage, et al., "Thin Films Containing Ceragenins Prevent Biofilm Formation on Endotracheal Tubes", 9th International Federation of Infection Control Congress, Oct. 14, 2008, pp. 1-1.
Papo et al., "Host peptides as new weapons in cancer treatment", CMLS Cell. Mol. Life Sci. 62 (2005), 784-790.
Paul B. Savage, et al: "Antibacterial Properties of cationic steroid antibiotics", FEMS Microbiology Letters, vol. 217, Nov. 2002, pp. 1-7.
Perry et al., "Assessing peri-implant tissue infection prevention in a percutaneous model", Journal of Biomedical Materials Research Part B: Applied Biomaterials, vol. 028, Nov. 19, 2009, pp. 397-408.
Piktel et al. Sporicidal Activity of Ceragenin CSA-13 Against Bacillus Subtillis, Scientific Reports, vol. 7, Mar. 15, 2017 [retrieved on Apr. 24, 2018. Retrieved from the internet: <URL: https://www.nature.com/articles/srep44452.pdf> Entire Document.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Pollard et al. (J Antimicrob Chemother 2012; 67:2665-2672).
Press release (Ceragenix Pharmaceuticals, Wayne State University, Brigham Young University, Systemic Anti-Infectives, Pre-clinical Title-Ceragenin (Trademark) Compound demonstrates potent activity against multidrug resistant bacterial strains of Pseudomonas, Denver, CO-Published Dec. 20, 2007).
Pycock, "The Dirty Mare", https://www.equine-reproduction.com/articles/DirtyMare.shtml, 2003.
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.
Examiner Interview Summary received for U.S. Appl. No. 14/208,082, mailed on Oct. 23, 2020, 4 pages.
Kuroda, et al., "Ceragenin CSA-13 induces cell cycle arrest and antipro liferative effects in wild-type and p52 null mutant HCT116 colon cancer cells", Preclinical Report, Wolters Kluwer Health 2013.

(56) References Cited

OTHER PUBLICATIONS

Xin-Zhong Lai, et al.," Ceragenins: Cholic Acid-Based Mimics of Antimicrobial peptides", Account of Chemical Research vol. 41, No. 10, Oct. 21, 2008, pp. 1233-1240.
Zanger et al., "Structure-Activity Relationship and Drug Design", Remington's Pharmaceutical Sciences, Chapter 27, 16th Edition, 1980, pp. 420-425.
Zaragoza Dorwald, Side Reactions in Organic Synthesis, 2005, WILEY-VCH Verlag GmbH & Co. KGaA, Weinheim, Preface. p. IX.
Shi et al., "Multi-center randomized double-blind clinicial trail on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sigma-Aldrich, Poly(ethylene-co-vinyl acetate), [Retrieved from internet <URL: http://www.sigmaaldrich.com/catalog/product/aldrich/340502?lang=- en®ion=US >], [Downloaded Jul. 22, 2016], excerpt in action.
Staphylococcal Infections (Electronic Resource; Merck Manual). Retrieved on Jul. 3, 2017: [http://www.merckmanuals.com/professional/infectious diseases/gram-positive-cocci/staphylococcal-infections].
Steeneveld et al. Cow-specific treatment of clinical mastitis: an economic approach. J. Diary. Sci. 94: 174-188, 2011.
Survey Research on Behcet's Disease, 2005 to 2007 Comprehensive Survey Reports, 2008, pp. 34-39.
Suzuki et al.; "Molecular Genetics of Plant Sterol Backbone Synthesis"; 2007; Lipids; 42: 47-54.
U.S. Appl. filed Apr. 22, 2016, Savage et al., U.S. Appl. No. 15/135,900.
U.S. Appl. filed Apr. 22, 2016, Savage et al., U.S. Appl. No. 15/135,928.
U.S. Appl. filed Apr. 22, 2016, Savage et al., U.S. Appl. No. 15/135,969.
U.S. Appl. filed Apr. 23, 2015, Beus et al., 14694028.
U.S. Appl. filed Apr. 7, 2017, Savage., U.S. Appl. No. 15/481,184.
U.S. Appl. filed Apr. 7, 2017, Savage., U.S. Appl. No. 15/481,884.
U.S. Appl. filed Aug. 19, 2015, Savage., U.S. Appl. No. 14/830,356.
U.S. Appl. filed Feb. 13, 2018, Genberg, et al., U.S. Appl. No. 15/895,848.
U.S. Appl. filed Jan. 16, 2017, Savage., U.S. Appl. No. 15/406,667.
U.S. Appl. filed Jan. 21, 2015, Savage., U.S. Appl. No. 14/602,071.
U.S. Appl. filed Jan. 22, 2015, Savage., U.S. Appl. No. 14/602,499.
U.S. Appl. filed Jul. 25, 2014, Savage, et al., U.S. Appl. No. 14/341,304.
U.S. Appl. filed Jun. 25, 2015, Genberg et al., U.S. Appl. No. 14/750,928.
U.S. Appl. filed Mar. 11, 2015, Beus et al., U.S. Appl. No. 14/644,946.
U.S. Appl. filed Mar. 11, 2015, Savage et al., U.S. Appl. No. 14/645,040.
U.S. Appl. filed Mar. 20, 2018, Savage et al., U.S. Appl. No. 15/926,577.
U.S. Appl. filed Mar. 20, 2018, Savage., U.S. Appl. No. 15/926,534.
U.S. Appl. filed Mar. 21, 2016, Beus et al., U.S. Appl. No. 15/076,313.
U.S. Appl. filed Mar. 23, 2018, Savage, Paul B., U.S. Appl. No. 15/934,534.
U.S. Appl. filed Mar. 23, 2018, Savage., U.S. Appl. No. 15/934,534.
U.S. Appl. filed Mar. 9, 2017, Savage et al., U.S. Appl. No. 15/454,135.
U.S. Appl. filed May 3, 2017, Savage et al., U.S. Appl. No. 15/585,632.
U.S. Appl. filed Oct. 16, 2014, Savage, et al., U.S. Appl. No. 14/515,858.
U.S. Appl. filed Oct. 30, 2014, Savage, et al., U.S. Appl. No. 14/398,094.
U.S. Appl. filed Oct. 6, 2015, Savage., U.S. Appl. No. 14/875,953.
U.S. Appl. filed Sep. 1, 2015, Genberg et al., U.S. Appl. No. 14/842,582.
U.S. Appl. filed Sep. 20, 2016, Genberg et al., U.S. Appl. No. 15/270,876.
U.S. Appl. filed Sep. 25, 2015, Savage., U.S. Appl. No. 14/866,213.
U.S. Appl. filed Sep. 9, 2015, Genberg et al., U.S. Appl. No. 14/848,819.
U.S. Appl. No. 13/841,549, filed Mar. 15, 2013, Office Action dated Apr. 23, 2015.
U.S. Appl. No. 14/288,126, filed May 27, 2014, Savage et al.
U.S. Appl. No. 14/926,738, filed Oct. 29, 2015, Vazquez et al.
U.S. Appl. No. 16/184,211, filed Nov. 8, 2018, Savage.
U.S. Application filed Feb. 17, 2015, by Savage, U.S. Appl. No. 14/624,200.
U.S. Application filed Mar. 10, 2015, by Darien et al., U.S. Appl. No. 14/642,905.
U.S. Application Filed on Jul. 29, 2014, by Vazquez et al., U.S. Appl. No. 14/364,283.
U.S. Application Filed on Oct. 1, 2015, by Savage et al., U.S. Appl. No. 14/873,013.
U.S. Application Filed on Oct. 25, 2016, by Vazquez et al., U.S. Appl. No. 15/333,514.
U.S. Patent Application filed Jul. 23, 2014 2014 by Vazquez et al., U.S. Appl. No. 14/339,342.
U.S. Patent Application Filed on Mar. 20, 2020, by Savage, U.S. Appl. No. 15/926,534.
US. Appl. filed Mar. 1, 2013, Savage., U.S. Appl. No. 13/783,007.
Valkonen, et al., "Bile acid amidoalcohols: simple organoqelators", Biosens Bioelectron, Dec. 2004.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.
Van Den Bogaard et al., "Antibiotic Usage in Animals: Impact on Bacterial Resistance and Public Health"; 1999; Drugs; 58 (4): 589-607.
Berge et al., Pharmaceutical salts. Journal of Pharmaceutical Sciences, vol. 66(1), pp. 1-19 (Year: 1977).
International Preliminary Report on Patentability received for PCT Patent Application No. PCT/US20/034297, mailed on Dec. 2, 2021, 6 pages.
Dennison et al., "Anticancer a-Helical Peptides and Structure/Function Relationships Underpinning their Interactions with Tumour Cell Membranes", Current Protein and Peptide Science, 2006, 7, No. 6, pp. 1-13.
Ding, et al., "Origins of cell selectivity of cationic steroid antibiotics", Journal of American Chemical Society, Oct. 2004, pp. 13642-13648.
International Search Report and Written Opinion received for PCT Patent Application No. PCT/US2020/034297, mailed on Aug. 26, 2020, 8 pages.
Papo et al., "Host defense peptides as new weapons in cancer treatment", Cmls Cellular and Molecular Life Sciences, vol. 62, No. 7-8, Apr. 1, 2005, pp. 784-790.
Sentamilselvi et al., International Journal of Trichology, vol. 1, Issue 2, pp. 100-108, Jul. 2009.

* cited by examiner

CSA-37

CSA-41

CSA-42

CSA-43

CSA-44

CSA-45

CSA-47

CSA-49

CSA-50

CSA-51

CSA-105

CSA-106

CSA-107

CSA-109

CSA-110

CSA-112

CSA-113

CSA-118

CSA-119

CSA-120

CSA-121

CSA-121a

CSA-122

CSA-123

CSA-124

CSA-130

CSA-131

CSA-132

Vehicle Control

M001  M002  M003  M004  M005  M006  M007  M008

CSA-44 (0.5%), Once Daily, 3 weeks

M017  M018  M019  M020  M021  M022  M023  M024

CSA-44 (2%), Once every other day, 3 weeks

M025  M026  M027  M028  M029  M030  M031  M032 ns directly aid in regenerating tissue, in particular in cases where the stimulated stem cells can differentiate into the types of cells needed to regenerate the targeted tissue. However, even in applications where the stem cells do not differentiate directly into the types of cells that make up the regenerated tissue, the enhanced secretion of growth factors can by itself promote tissue regeneration.

USE OF CSA COMPOUNDS TO STIMULATE STEM CELLS AND HAIR GROWTH

CROSS-REFERENCE TO RELATED APPLICATION

This Application claims the benefit of U.S. Provisional Patent Application No. 62/852,110, filed May 23, 2019, which is incorporated by reference in its entirety.

BACKGROUND

Tissue damage can occur as a result of several conditions such as injury, disease, a genetic condition or predisposition, infection, inflammation, stress, or an autoimmune reaction. The body utilizes stem cells to grow and maintain its tissues. However, tissue degradation cannot always be avoided or reversed simply by relying on self-activation of endogenous stem cells. Often, damaged tissue cannot regenerate because tissue stem cells are not stimulated and therefore fail to promote regeneration and maintenance of the associated tissues.

One particular form of tissue degradation is hair loss. For animals that spend many hours outdoors, such as livestock animals, hair loss may make exposed areas of skin more susceptible to sunburn, insect bites, irritation, and the like. In humans, hair thinning and baldness may cause psychological distress due to their effect on appearance.

Where an underlying infection and/or inflammation is associated with hair loss or other tissue damage, treatment of hair loss or tissue damage typically includes treating the underlying infection and waiting form hair and/or tissue growth to resume naturally. Although hair and/or tissue growth often resumes once the underlying condition has been treated, it may take an extended amount of time for the hair and/or tissue to grow back to pre-infection thickness and health. Where hair and/or tissue loss has other causes, treatment options may include medication (such as minoxidil, often sold under the trade name Rogaine® or Regaine®), corticosteroid injection, hormonal modulation, immunosuppressants, hair transplant surgery, or using cosmetic articles such as wigs.

Although stem cell therapy has been known for some time, several limitations remain to effective and targeted use for regenerating tissues. Stem cells are notoriously difficult to collect or stimulate. Accordingly, there remains a need for improved compositions and methods for stimulating stem cells to promote the regeneration of targeted tissues and/or to prevent tissue degradation.

BRIEF SUMMARY

The present disclosure describes methods of regenerating tissue and/or preventing tissue atrophy or degradation by administering one or more cationic steroidal antimicrobial (CSA) compounds. In embodiments, a method comprises: (1) providing a tissue regeneration composition (i.e., treatment composition) including one or more CSA compounds and a carrier; (2) applying the tissue regeneration composition to a subject in need thereof; and (3) the tissue regeneration composition stimulating the regeneration of tissue in the subject.

The tissue regenerating properties of the compositions described herein are believed to be due at least in part to their ability to promote the proliferation and migration of stem cells, the production of growth factors by the stem cells, or both. The proliferation of stem cells may in some applications directly aid in regenerating tissue, in particular in cases where the stimulated stem cells can differentiate into the types of cells needed to regenerate the targeted tissue. However, even in applications where the stem cells do not differentiate directly into the types of cells that make up the regenerated tissue, the enhanced secretion of growth factors can by itself promote tissue regeneration.

The tissue regeneration composition may be administered via any suitable route of administration such as topically, orally, rectally, transdermally, via inhalation, or via injection. In embodiments, the treatment composition is formulated as a cream, salve, lotion, liquid solution, spray, soap, shampoo, or other such formulation readily administrable in a topical application.

In preferred embodiments, the tissue regeneration composition comprising one or more CSA compounds is applied directly to targeted tissue to stimulate local stem cells and thereby promote tissue regeneration. The stimulated stem cells may therefore be tissue (i.e., "adult") stem cells such as mesenchymal stem cells (i.e., "stromal cells") or tissue-specific stem cells such as follicular stem cells, hematopoietic stem cells, neural stem cells, epithelial stem cells (e.g., in the gut or skin), or other such stem cells found in bone marrow, peripheral blood, brain, spinal cord, dental pulp, blood vessels, skeletal muscle, epithelia of the skin and digestive system, cornea, retina, liver, and pancreas, for example. Direct application of a tissue regeneration composition to targeted tissue has surprisingly been found to effectively provide direct tissue stem cell stimulation and corresponding tissue regeneration without the need to separately harvest and potentiate stem cells.

In contrast, stem cells may be separately collected or harvested, then treated with and/or mixed with a treatment composition comprising one or more CSA compounds, and then applied to targeted tissue. Alternatively, a stem cell culture may be treated with a treatment composition comprising one or more CSA compounds, and then conditioned media from the stem cell culture may be applied to a targeted tissue. Such embodiments may utilize tissue stem cells as described above (e.g., collected from umbilical cord tissue, bone marrow, adipose, and/or the targeted tissue type itself), induced pluripotent stem cells, and/or embryonic stem cells.

In one embodiment, the targeted tissue is hair-generating dermal tissue, and a tissue regeneration composition is administered so as to regenerate hair follicles and thereby stimulate hair growth. A method of stimulating hair growth may comprise: (1) providing a tissue regeneration composition including one or more CSA compounds and a carrier; (2) applying the tissue regeneration composition to a subject experiencing or at risk of experiencing hair loss; and (3) the tissue regeneration composition stimulating hair growth and/or preventing hair loss in the subject.

In embodiments, a tissue regeneration composition is applied to an anatomical target that is infected with a microbial infection, such as to a target having a fungal and/or bacterial infection. In such an implementation, the antimicrobial activity of the composition may further promote tissue regeneration at the infected site by removing the underlying microbial load that may be contributing to tissue damage and/or preventing desired tissue growth. Even without the antimicrobial effects, however, it has been found that the growth stimulating effects of the disclosed treatments function independently of the antimicrobial effects of the treatment.

In embodiments, a tissue regeneration composition is applied to treat hair loss associated with a fungal infection or other microbial infection. In such an implementation, the antimicrobial activity of the composition may assist in hair growth by removing an underlying infection causing hair loss. However, it has been found that the hair growth stimulating effects of the disclosed treatments act in addition to, and function independently of, any antimicrobial effects of the treatment.

In presently preferred embodiments, treatment compositions used to stimulate tissue regeneration and/or prevent tissue atrophy include CSAs having hydrolysable (e.g., ester) linkages. CSA compounds of this type are generally less costly to manufacture. In addition, such CSA compounds provide desired activity when applied or administered, but then naturally hydrolyze and degrade to an inactive form as a matter of course, thereby minimizing concerns related to long-term exposure and/or environmental exposure.

Any CSA compound described herein, or any combination of such CSA compounds may be utilized in a treatment composition. In preferred embodiments, the treatment composition includes one or more CSA compounds having hydrolysable linkages. Exemplary CSA compounds include CSA-44, CSA-142, CSA-144, CSA-145, CSA-146, and CSA-148, in particular, CSA-44, CSA-142, CSA-144, and CSA-148. Alternatively, CSA-13 has shown effectiveness but does not contain hydrolysable linkages. Compounds such CSA-131, CSA-192, CSA-255, and CSA-256 would also be expected to stimulate tissue regeneration but do not include readily hydrolysable linkages. CSA-13 and CSA-131 are more stable than CSA-192, CSA-255, and CSA-256, which are more stable than CSAs having hydrolysable linkages.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just example embodiments and are not to be considered to be limiting in scope, various embodiments will be described and explained with additional specificity and detail through the use of the accompanying drawings in which.

DETAILED DESCRIPTION

Figure 1A:
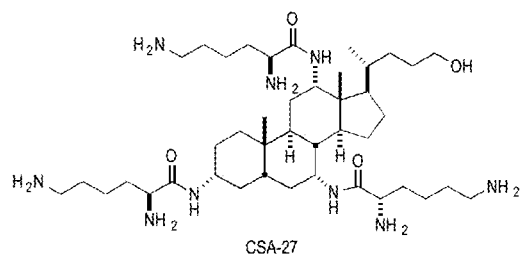
FIG. 1A illustrates examples of cationic steroidal antimicrobial compounds having ester or amide linkages at one or more of the $R_3$, $R_7$, and $R_{12}$ positions.
Figure 1A:
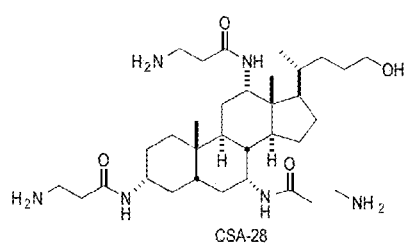
Figure 1A:
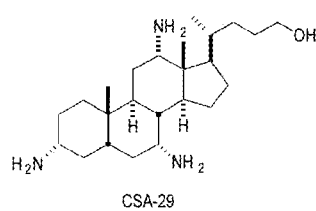
Figure 1A:
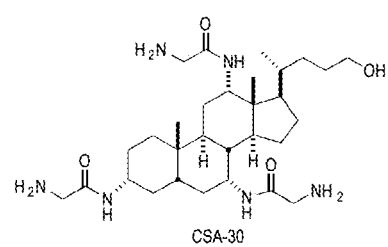
Figure 1A:
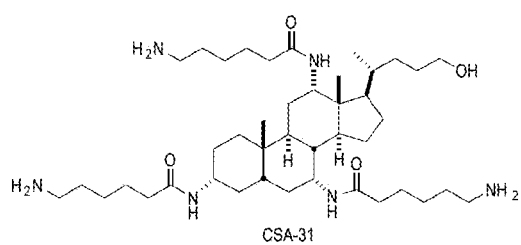
Figure 1A:
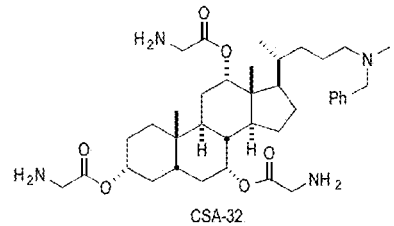
Figure 1A:
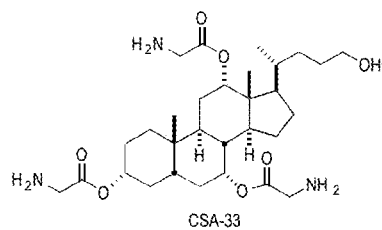
Figure 1A:
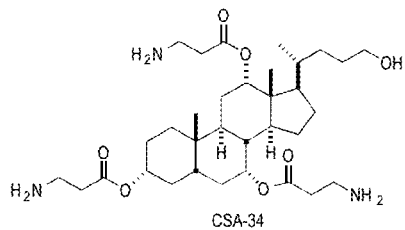
Figure 1A:
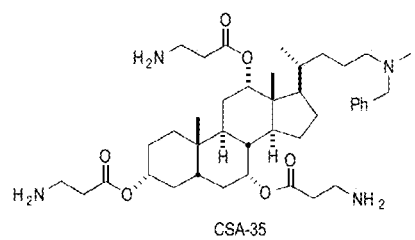
Figure 1A:
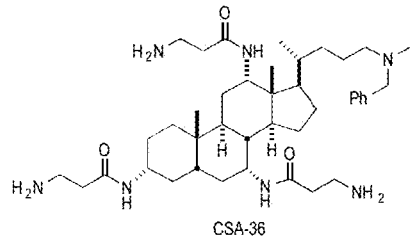
Figure 1A:
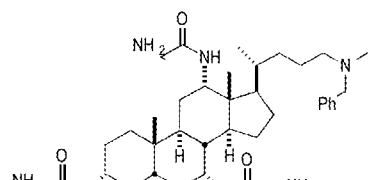
Figure 1A:
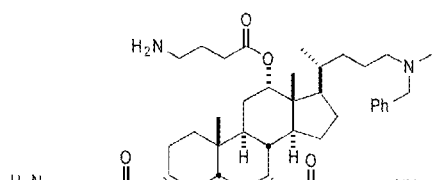
Figure 1A:
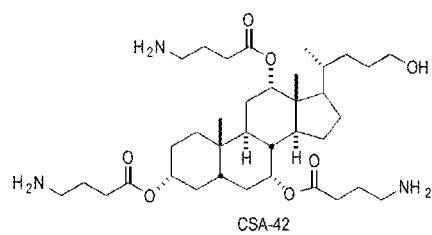
Figure 1A:
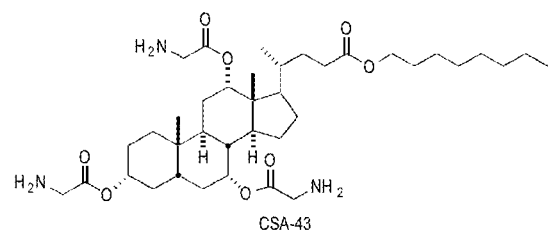
Figure 1A:
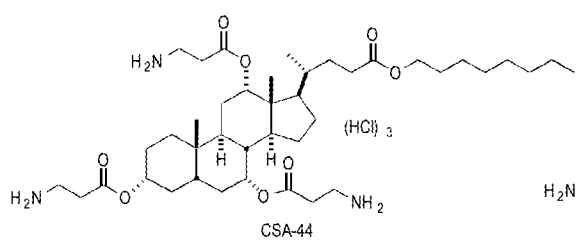
Figure 1A:
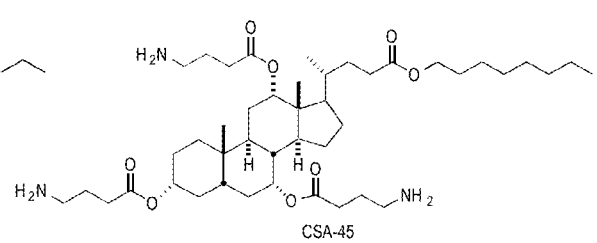
Figure 1A:
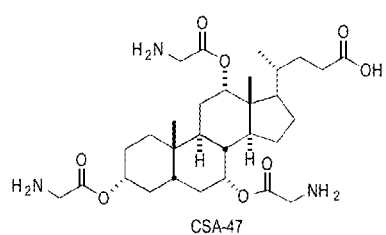
Figure 1A:
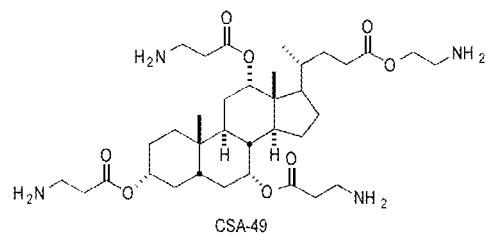
Figure 1A:
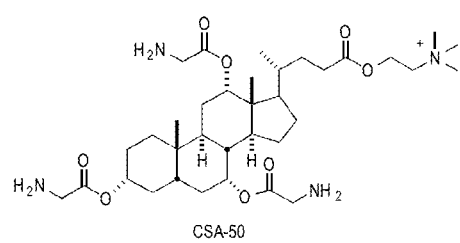
Figure 1A:
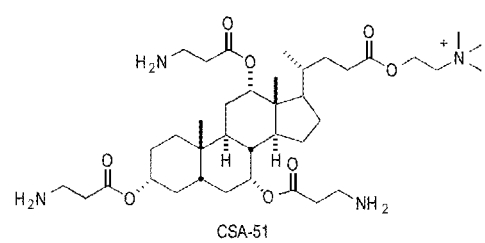
Figure 1A:
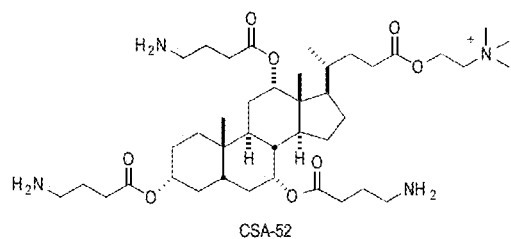
Figure 1A:
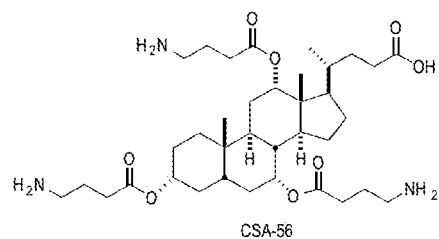
Figure 1A:
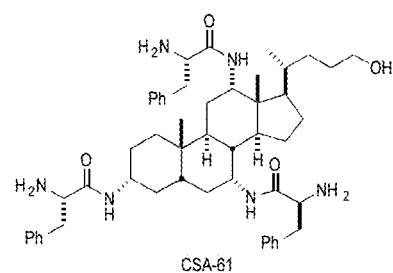
Figure 1A:
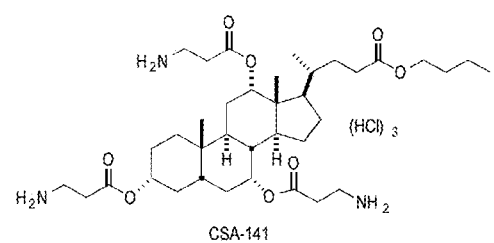
Figure 1A:
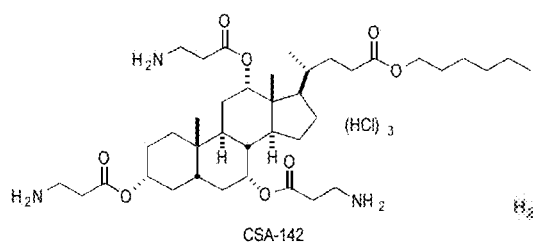
Figure 1A:
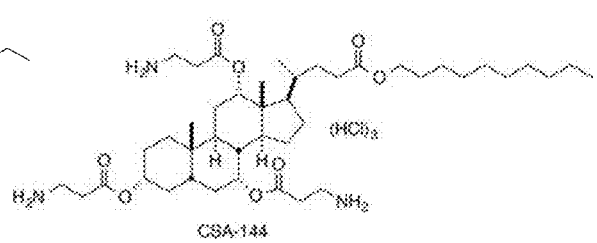
Figure 1A:
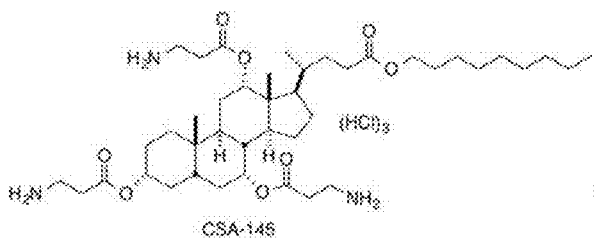
Figure 1A:
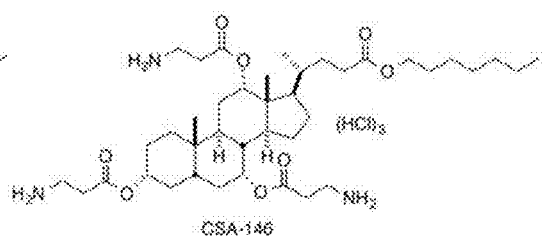
Figure 1A:
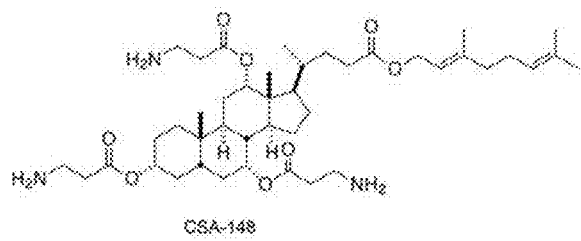

The embodiments disclosed herein will now be described by reference to more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

I. OVERVIEW OF CSA COMPOUNDS

Cationic steroidal anti-microbial (CSA) compounds, also referred to as "CSA compounds", "CSAs", CSA molecules or "ceragenin" compounds, are synthetically produced, small molecule chemical compounds that include a sterol backbone having various charged groups (e.g., amine and cationic groups) attached to the backbone. The sterol backbone can be used to orient amine or guanidine groups on a face or plane of the sterol backbone. CSAs are cationic and amphiphilic, based upon the functional groups attached to the backbone. They are facially amphiphilic with a hydrophobic face and a polycationic face.

Without wishing to be bound to any particular theory, it is theorized that the CSA compounds described herein act as antimicrobial agents (e.g., anti-bacterial, anti-fungal, and/or anti-viral agents) by binding to the cellular membrane of bacteria and other microbes and inserting into the cell membrane, forming a pore that allows the leakage of ions and cytoplasmic materials that are critical to the microbe's survival, thereby leading to the death of the affected microbe.

Unexpectedly, the use of CSA compounds has also been found to stimulate stem cells and thereby promote tissue regeneration independent of the antimicrobial properties of the compounds. One particular application of stimulating stem cells and regenerating tissue is in treating hair loss. Even in circumstances where the hair loss is associated with an underlying infection, administration of one or more CSA compounds was found to promote regeneration of hair follicles independent of treating the underlying infection. For example, compared to use of traditional topical antimicrobial compounds to treat a skin infection, use of CSA compounds resulted in hair growing back faster and thicker.

An example of a CSA compound is shown below as Formula I. As will be discussed in greater detail below, the R groups of Formula I can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring). Typically, the A, B, and C rings are 6-member rings while the D ring is a 5-member ring.

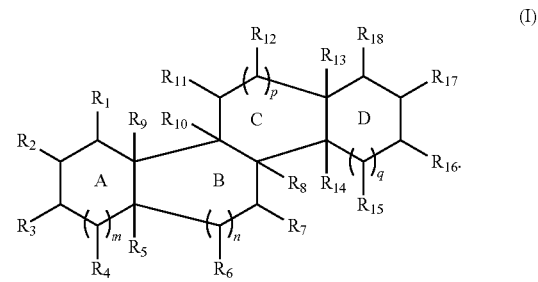

(I)

The CSA compounds can have a structure of Formula II, Formula III, or Formula IV:

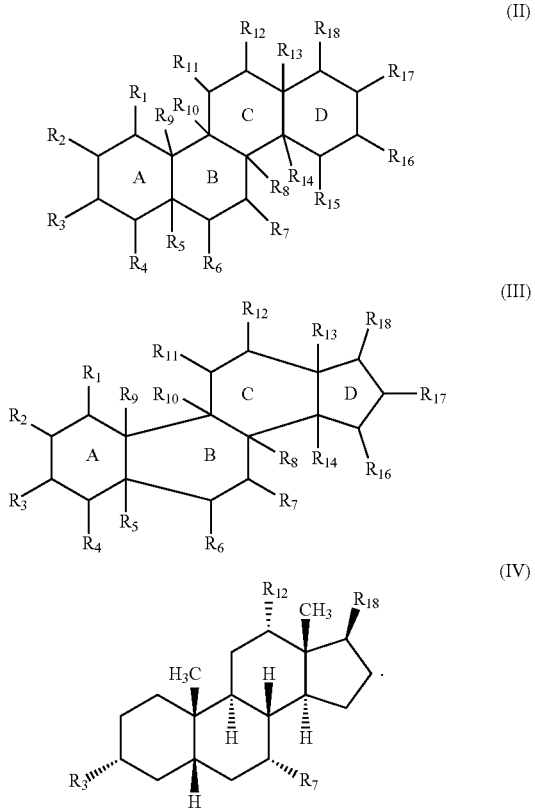

Definitions for the R groups are set forth below. Formula II is a subset of Formula I in which rings A, B, C, and D are 6-member rings. Formula III is a subset of Formula I in which rings A, B, and C are 6-member rings and D is a 5-member ring. Formula IV is a subset of Formula III in which the stereochemistry is defined and the R groups other than R3, R7, $R_{12}$, and R18 are defined as either hydrogen or methyl.

Figure 1B:
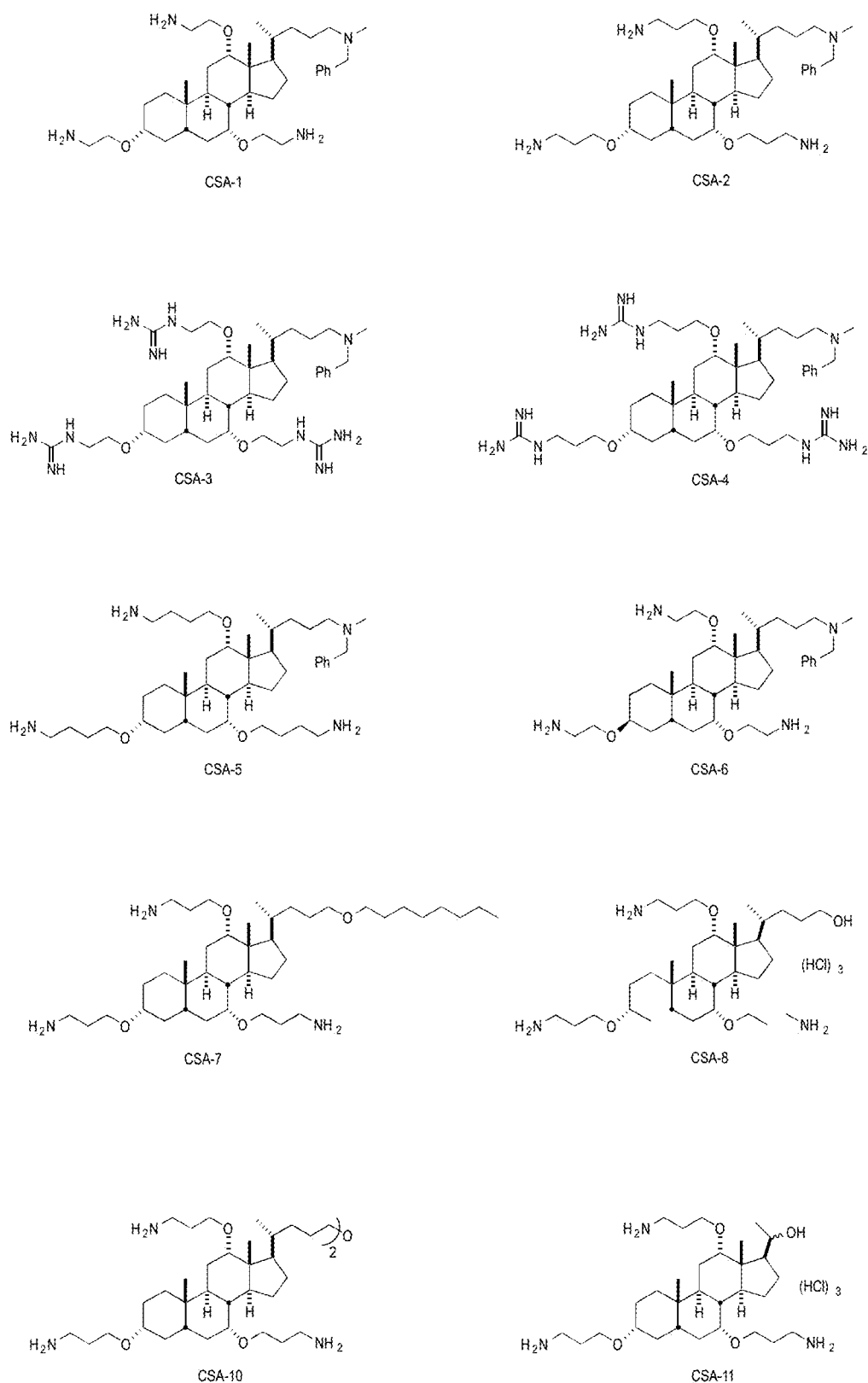
FIG. 1B illustrates examples of cationic steroidal antimicrobial compounds having ether linkages at one or more of the $R_3$, $R_7$, and $R_{12}$ positions.
Figure 1B:
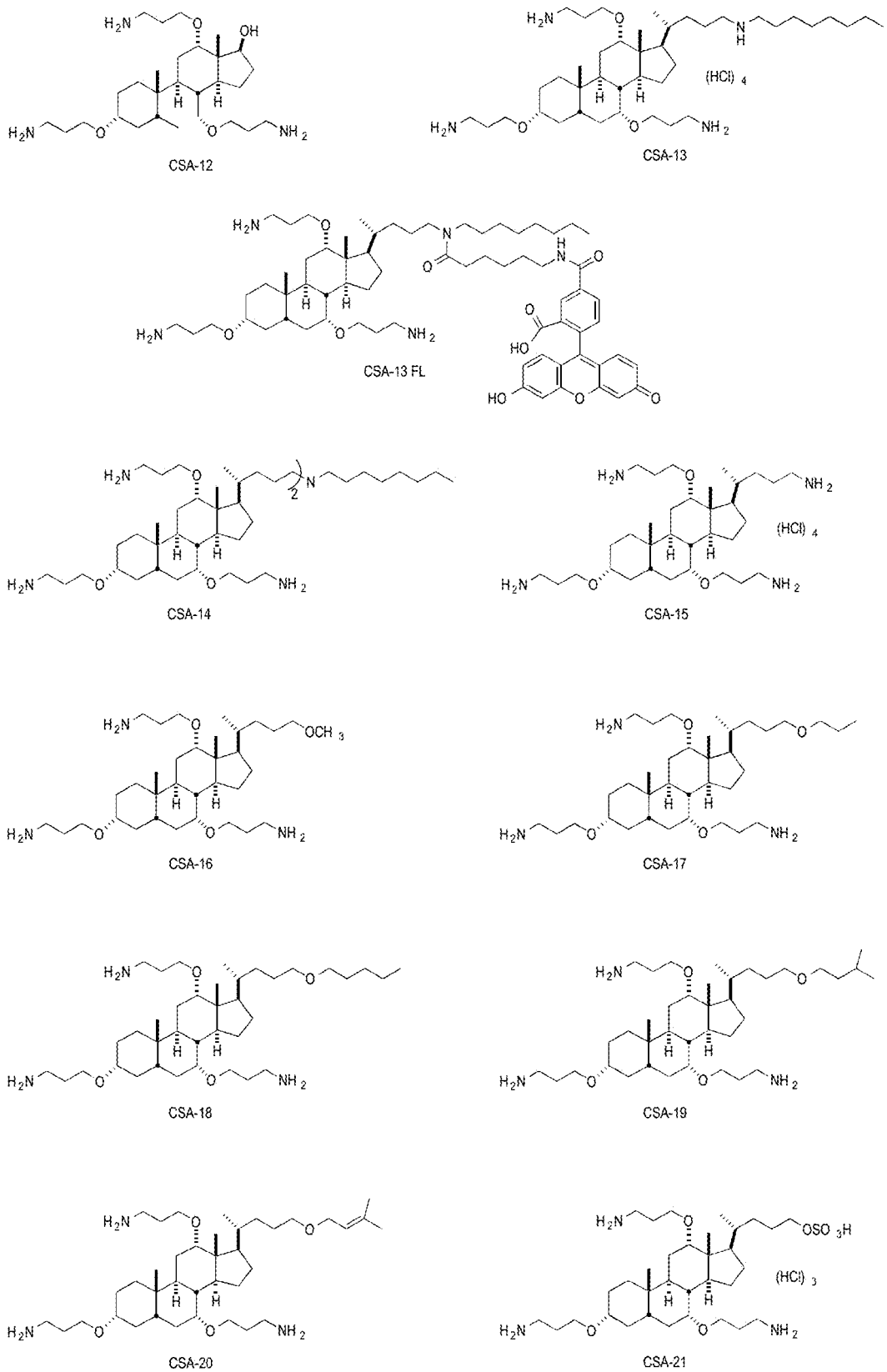
Figure 1B:
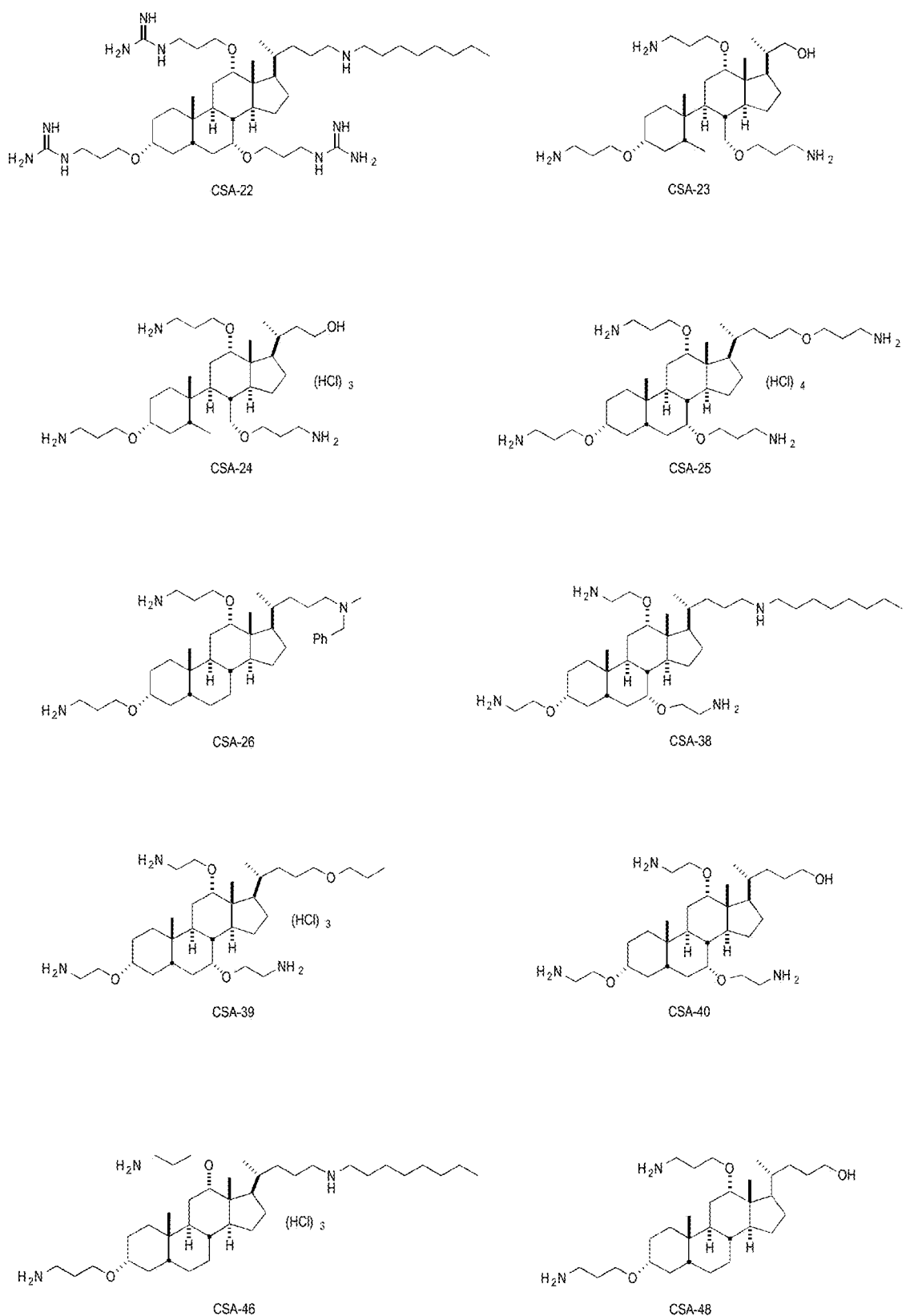
Figure 1B:
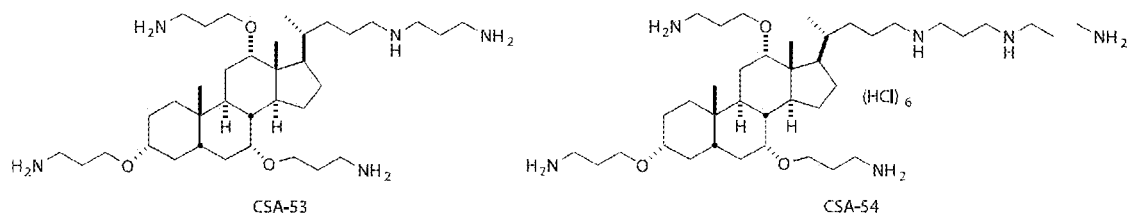
Figure 1B:
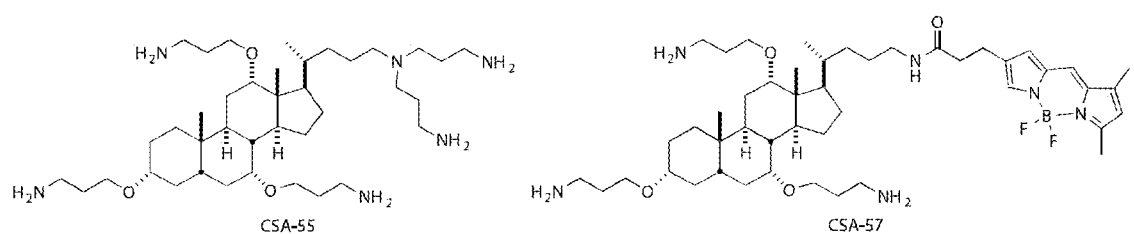
Figure 1B:
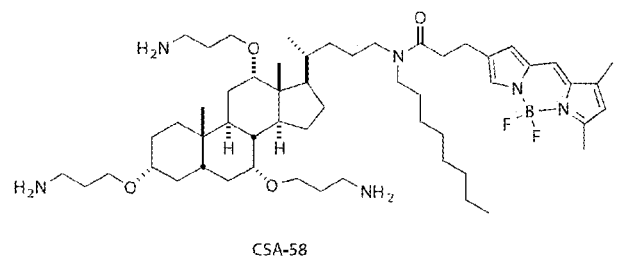
Figure 1B:
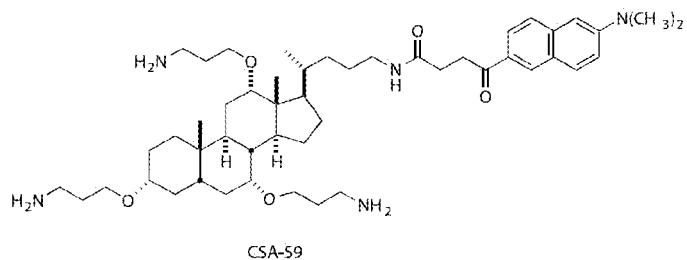
Figure 1B:
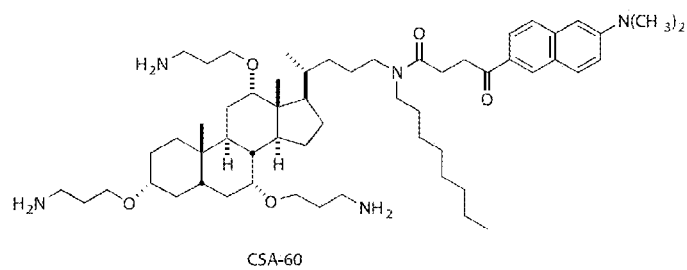
Figure 1B:
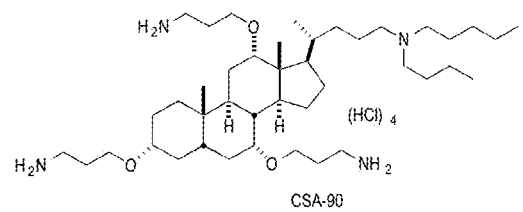
Figure 1B:
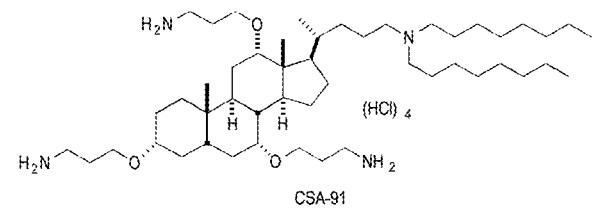
Figure 1B:
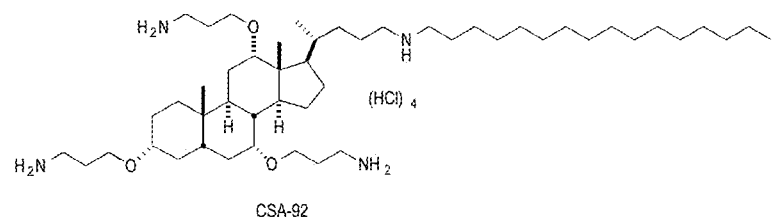
Figure 1B:
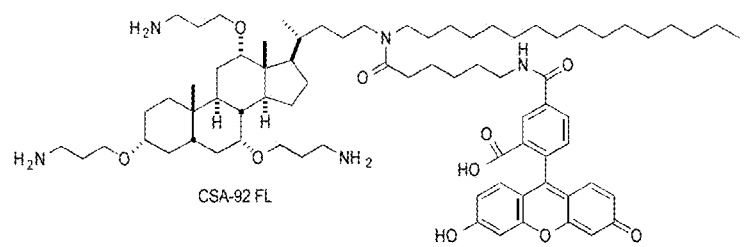
Figure 1B:
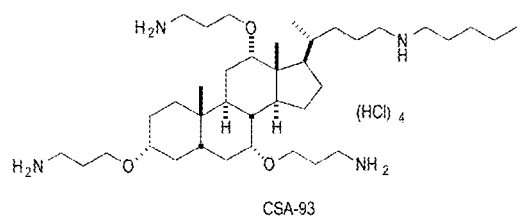
Figure 1B:
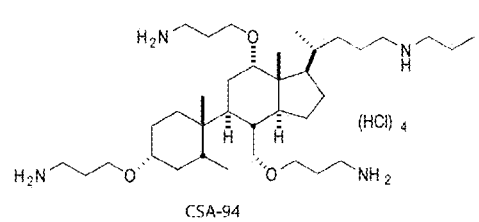
Figure 1B:
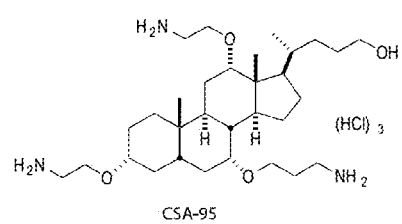
Figure 1B:
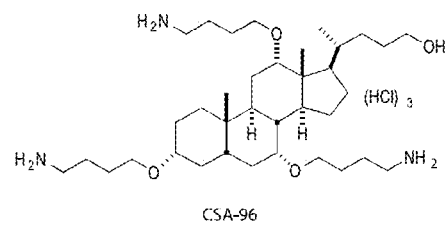
Figure 1B:
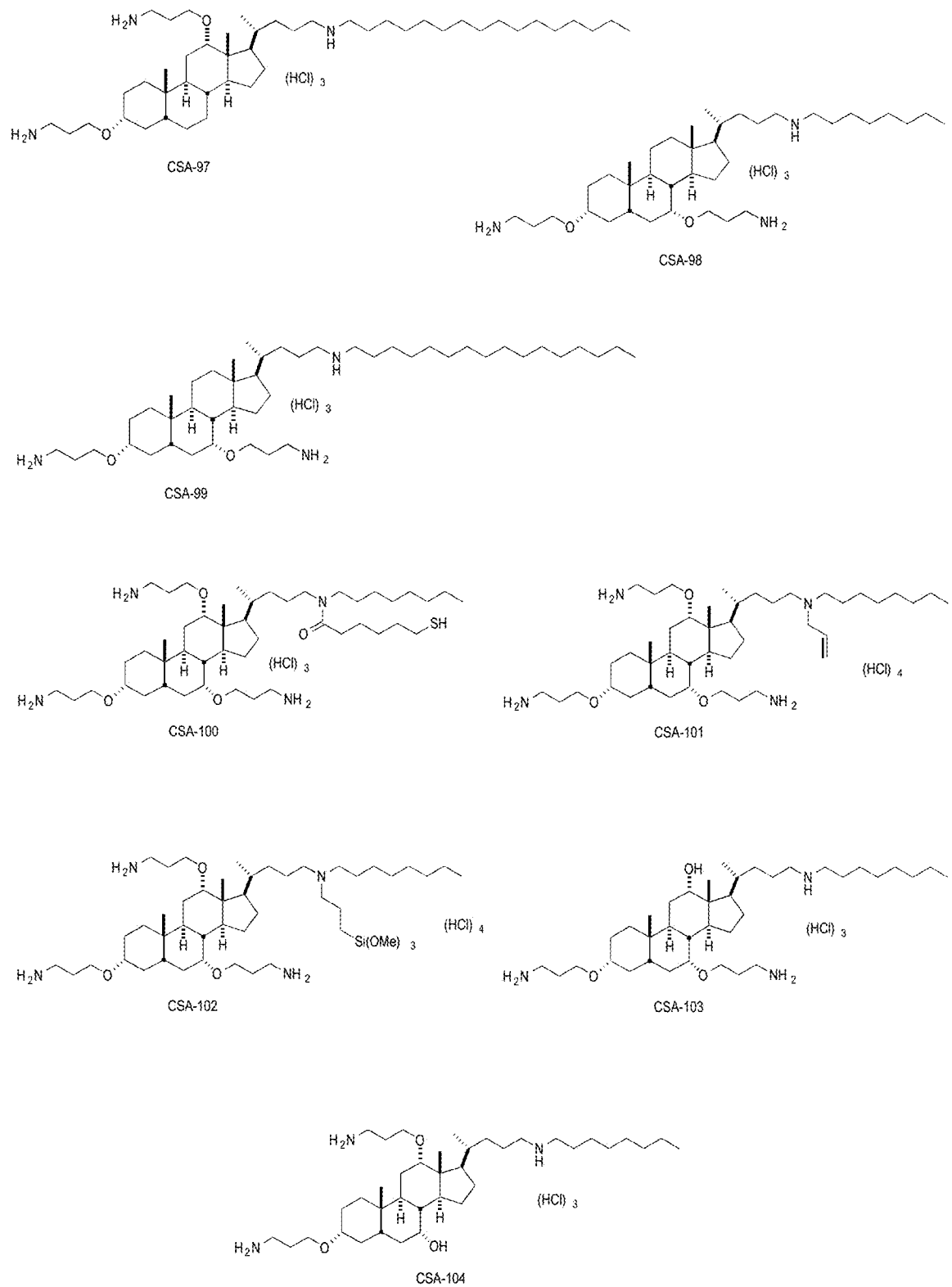
Figure 1B:
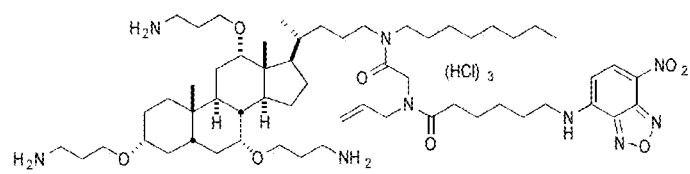
Figure 1B:
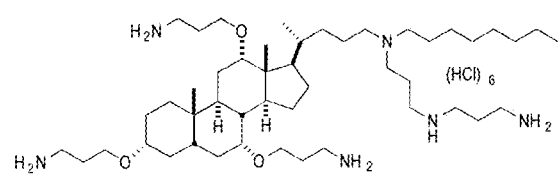
Figure 1B:
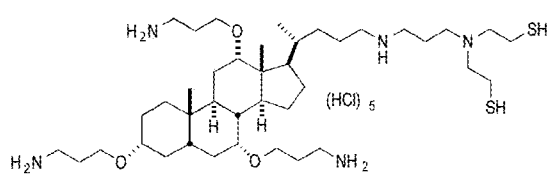
Figure 1B:
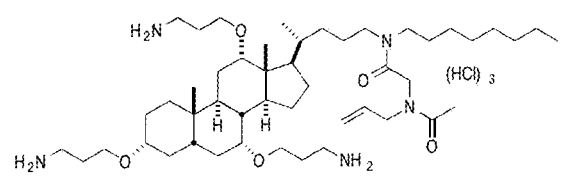
Figure 1B:
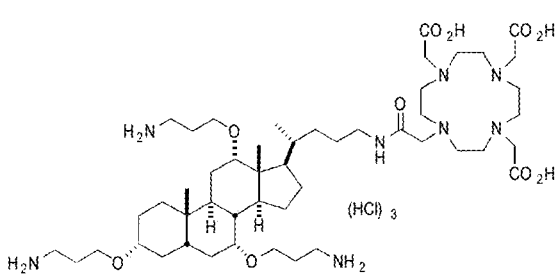
Figure 1B:
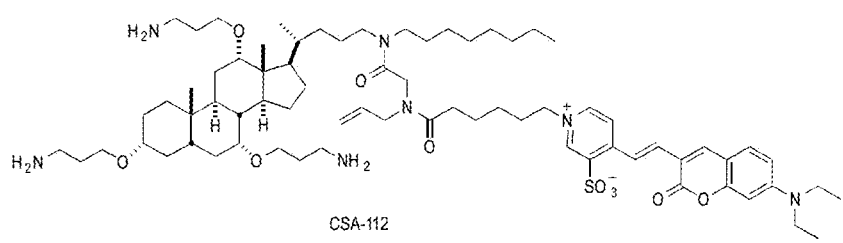
Figure 1B:
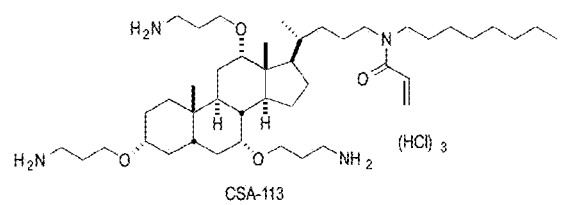
Figure 1B:
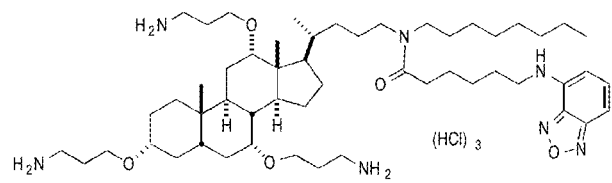
Figure 1B:
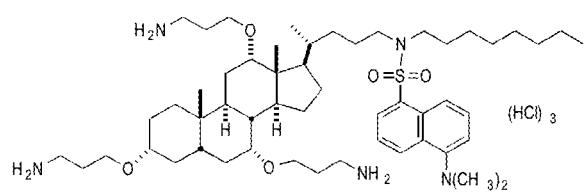
Figure 1B:
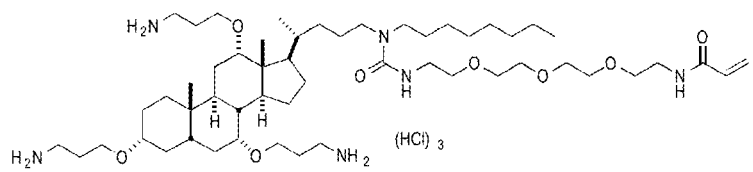
Figure 1B:
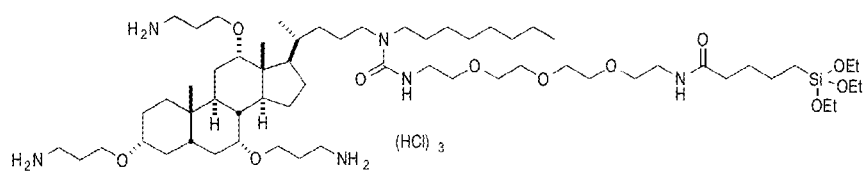
Figure 1B:
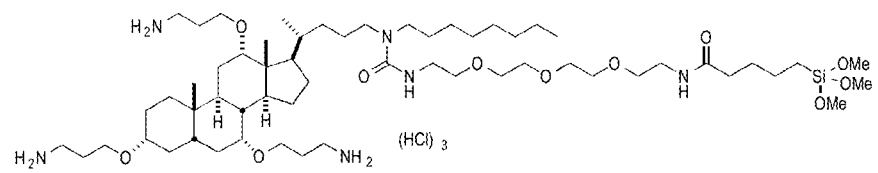
Figure 1B:
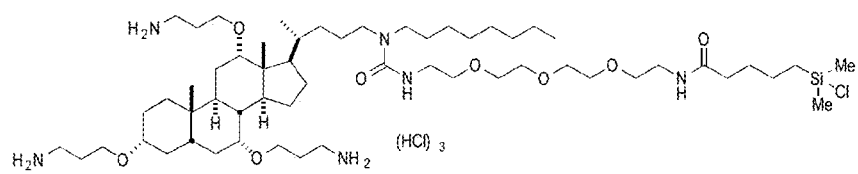
Figure 1B:
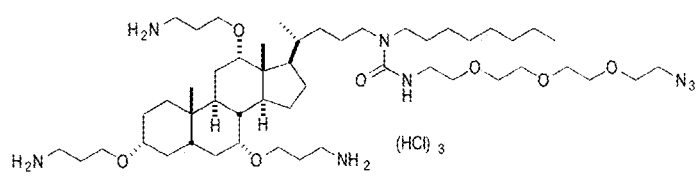
Figure 1B:
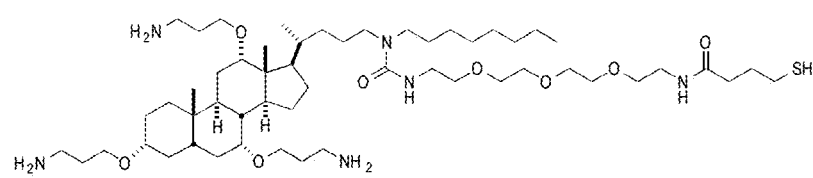
Figure 1B:
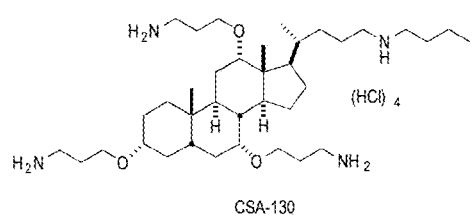
Figure 1B:
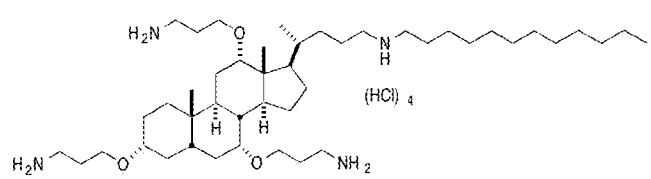
Figure 1B:
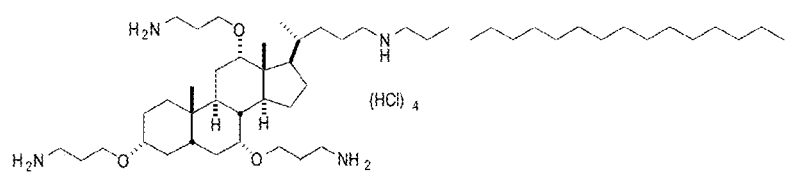
Figure 1B:
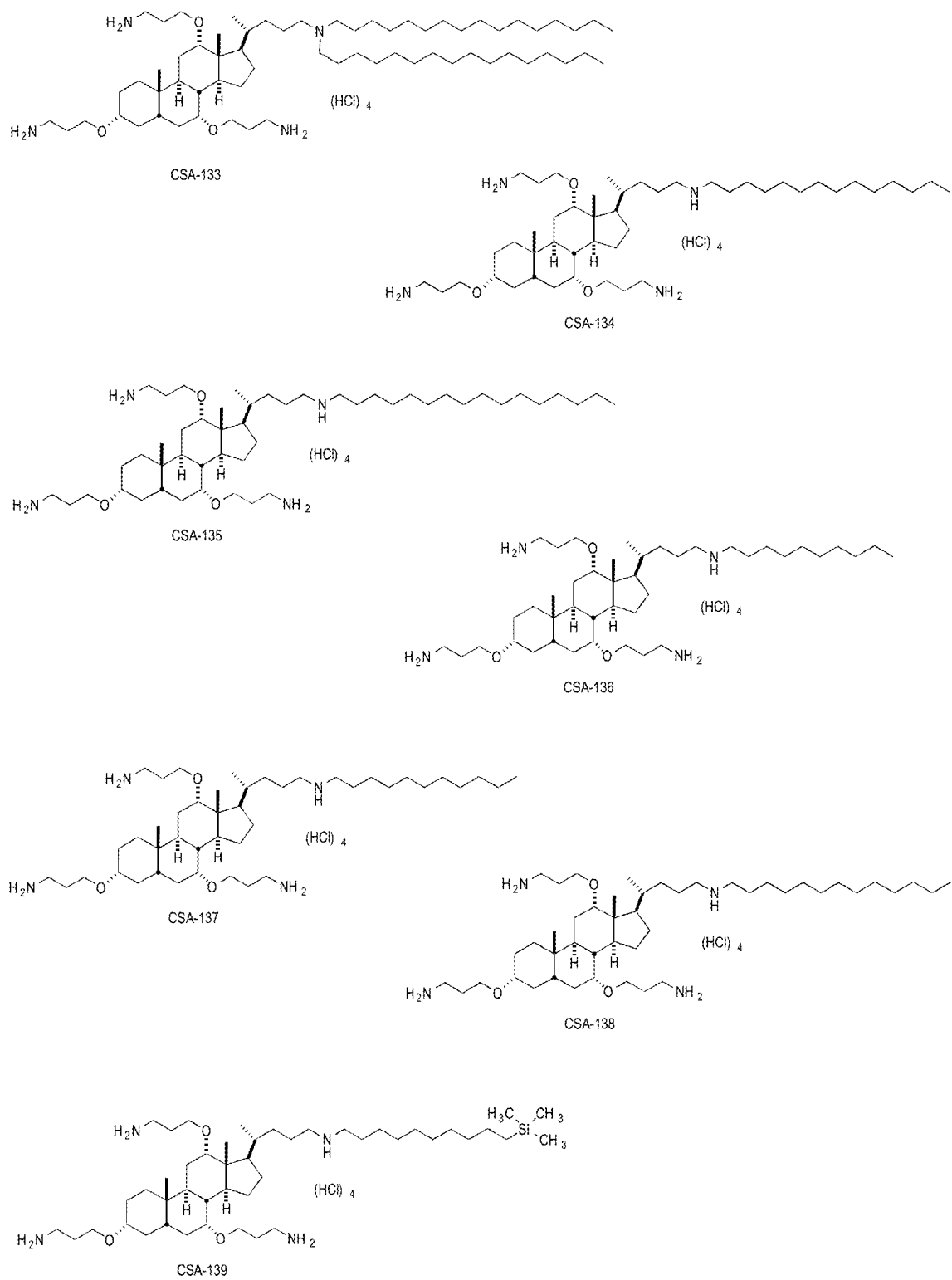
Figure 1C:
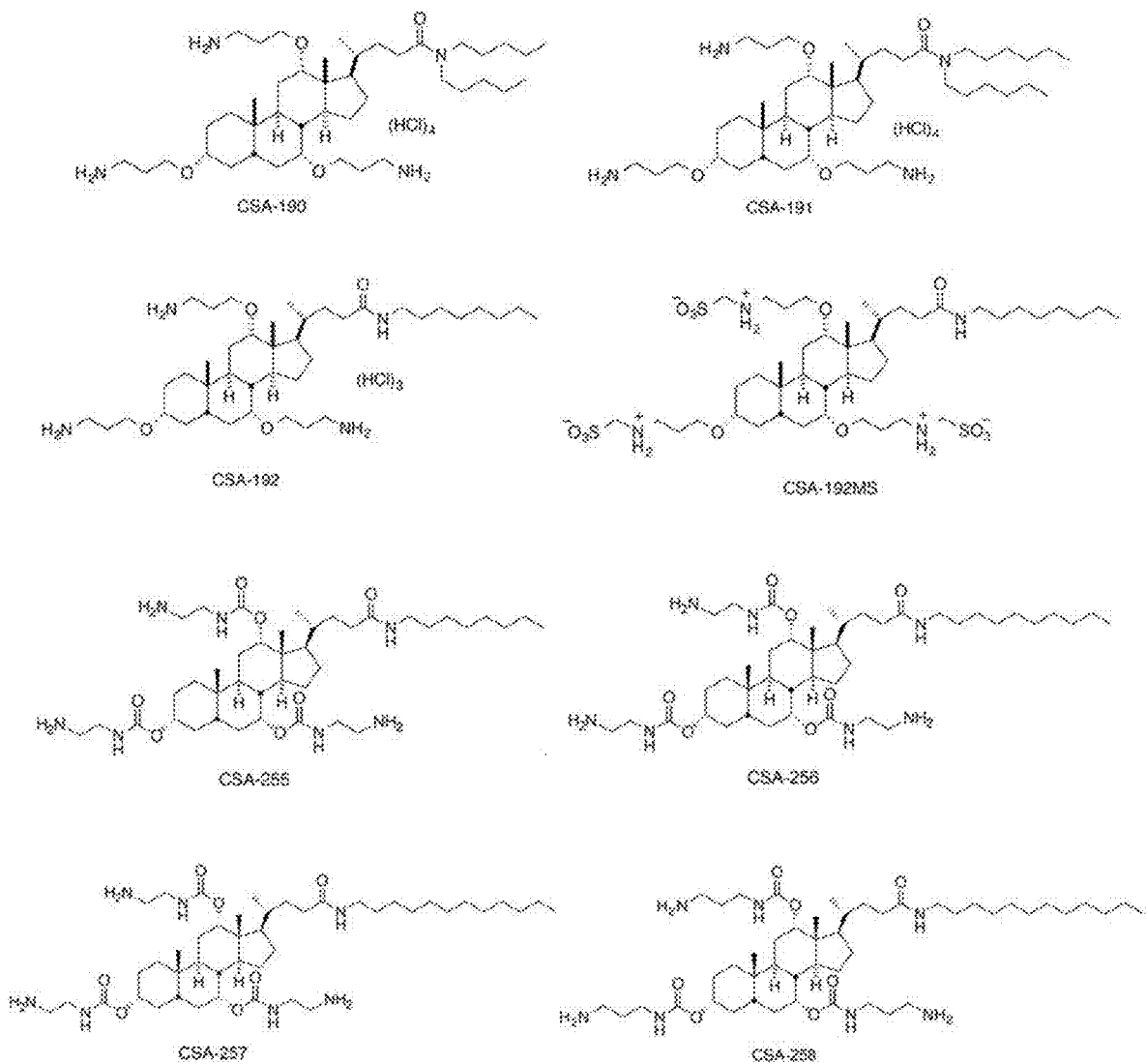
FIG. 1C illustrate example cationic steroidal antimicrobial compounds having an amide linkage within the $R_{18}$ group and ether or urethane linkages at the $R_3$, $R_7$, and $R_{12}$ positions.

A number of examples of CSA compounds of Formula I, Formula II, Formula III, and Formula IV that can be utilized to stimulate stem cells are illustrated in FIGS. 1A-1C.

Typically, CSAs used herein are of two types: (1) CSAs having cationic groups linked to the sterol backbone with hydrolysable linkages and (2) CSAs having cationic groups linked to the sterol backbone with non-hydrolysable linkages. For example, one type of hydrolysable linkage is an ester linkage, and one type of non-hydrolysable linkage is an ether linkage. CSAs of the first type can be "inactivated" by hydrolysis of the linkages coupling the cationic groups to the sterol backbone, whereas CSAs of the second type are more resistant to degradation and inactivation.

A number of examples of CSA compounds that may be used in the embodiments described herein are illustrated in FIGS. 1A-1C. Non-limiting examples of CSAs with hydrolysable linkages are set forth in FIG. 1A and include CSA-27, CSA-28, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-141, CSA-142, CSA-144, CSA-145, CSA-146, CSA-148.

Non-limiting examples of CSAs with non-hydrolysable linkages are set forth in FIG. 1B and include CSA-13, CSA-90, CSA-131, CSA-136, CSA-137, and CSA-138.

Non-limiting examples of CSAs with both hydrolysable and non-hydrolysable linkages are set forth in FIG. 1C and include CSA-190, CSA-191, CSA-192, CSA-255, CSA-256, and CSA-257.

In presently preferred embodiments, treatment compositions used to stimulate hair growth and/or prevent hair loss are CSAs with hydrolysable (e.g., ester) linkages. CSA compounds of this type are generally less costly to manufacture. In addition, such CSA compounds provide desired activity when applied or administered, but then naturally hydrolyze and degrade to an inactive form as a matter of course, thereby minimizing concerns related to long term exposure and/or environmental exposure.

In Formula I, Formula II, Formula III, and Formula IV, at least two of $R_3$, $R_7$, or $R_{12}$ may independently include a cationic moiety attached to the sterol backbone via hydrolysable (e.g., ester) or non-hydrolizable (e.g., ether) linkages. A tail moiety is usually attached to Formula I at $R_{18}$. The tail moiety may be charged, uncharged, polar, non-polar, hydrophobic, or amphipathic, for example, and can thereby be selected to adjust the properties of the CSA and/or to provide desired characteristics.

The activity of the CSA compounds can be affected by the orientation of the substituent groups attached to the backbone structure. In one embodiment, the substituent groups attached to the backbone structure are oriented on a single face of the CSA compound. Accordingly, each of $R_3$, $R_7$, and $R_{12}$ may be positioned on a single face of Formula I, Formula II, Formula III, and Formula IV. In addition, Rig may also be positioned on the same single face.

II. STIMULATION OF STEM CELLS USING CSA COMPOUNDS

Embodiments described herein are directed to methods of regenerating tissue and/or preventing tissue atrophy or degradation in a subject. In embodiments, a method comprises: (1) providing a tissue regeneration composition (i.e., treatment composition) including one or more CSA compounds and a carrier; (2) applying the tissue regeneration composition to a subject in need thereof; and (3) the tissue regeneration composition stimulating the regeneration of tissue in the subject.

In one embodiment, the targeted tissue is hair-generating dermal tissue, and a tissue regeneration composition is administered so as to regenerate hair follicles and thereby stimulate hair growth. In embodiments, a method comprises: (1) providing a tissue regeneration composition including one or more CSA compounds and a carrier; (2) applying the tissue regeneration composition to a subject in need thereof; and (3) the tissue regeneration composition stimulating hair growth and/or preventing hair loss in the subject.

Other therapeutic uses may include regenerating tissue damaged as a result of cancer treatment (e.g., non-Hodgkin's lymphoma, leukemia), stroke, osteoarthritis, autoimmune diseases such as rheumatoid arthritis, spinal cord injuries, brain injuries, cardiac injuries or disorders, and type I diabetes, for example.

In preferred embodiments, the tissue regeneration composition comprising one or more CSA compounds is applied directly to targeted tissue to stimulate local stem cells and thereby promote tissue regeneration. The stimulated stem cells may therefore be tissue (i.e., "adult") stem cells such as mesenchymal stem cells (i.e., "stromal cells") or tissue-specific stem cells such as follicular stem cells, hematopoietic stem cells, neural stem cells, epithelial stem cells (e.g., in the gut or skin), or other such stem cells found in bone marrow, peripheral blood, brain, spinal cord, dental pulp, blood vessels, skeletal muscle, epithelia of the skin and digestive system, cornea, retina, liver, and pancreas, for example. Direct application of a tissue regeneration composition to targeted tissue has surprisingly been found to effectively provide direct tissue stem cell stimulation and corresponding tissue regeneration without the need to separately harvest and potentiate stem cells.

In contrast, stem cells may be separately collected or harvested, then treated with and/or mixed with a treatment composition comprising one or more CSA compounds, and then applied to targeted tissue. Alternatively, a stem cell culture may be treated with a treatment composition comprising one or more CSA compounds, and then conditioned media from the stem cell culture may be applied to a targeted tissue. Such embodiments may utilize tissue stem cells as described above (e.g., collected from umbilical cord tissue, bone marrow, adipose, and/or the targeted tissue type itself), induced pluripotent stem cells, and/or embryonic stem cells.

Though embodiments involving a separate stem cell collection step are included within the general scope of this disclosure, they are less preferred than methods that allow direct application of the treatment composition to the targeted tissue because they necessarily require additional steps of collecting or harvesting stem cells, mixing or activating the collected stem cells, and in some cases culturing the stem cells and collecting a conditioned media.

The tissue regenerating properties of the compositions described herein are believed to be due at least in part to their ability to promote the proliferation and migration of stem cells, the production of growth factors by the stem cells, or both. The proliferation of stem cells may in some applications directly aid in regenerating tissue, in particular in cases where the stimulated stem cells can differentiate into the types of cells needed to regenerate the targeted tissue. However, even in applications where the stem cells do not differentiate directly into the types of cells that make up the regenerated tissue, the enhanced secretion of growth factors can by itself promote tissue regeneration.

Without being bound to any particular theory, it is believed that CSA compounds are capable of modulating one or more cellular receptors such as formyl peptide receptor-like 1 (FPRL1) and/or other G-protein-coupled receptors. This can induce various signaling pathways such as enhanced expression of early growth response 1 (EGR1) and enhanced activation of mitogen-activated protein kinases (MAPKs), leading to stem cell stimulating effects such as enhanced proliferation and migration of stem cells, enhanced production of extracellular growth factors, enhanced paracrine and/or endocrine signaling, or combination thereof.

The tissue regeneration composition may be administered via any suitable route of administration such as topically, orally, rectally, transdermally, via inhalation, or via injection. In embodiments, the treatment composition is formulated as a cream, salve, lotion, liquid solution, spray, soap, shampoo, or other such formulation readily administrable in a topical application.

In embodiments, a treatment composition is applied to treat tissue that has a microbial infection such as a fungal or bacterial infection. In such an implementation, the antimicrobial activity of the composition may indirectly promote tissue regeneration by lessening or removing the underlying infectious burden on the targeted tissue. However, it will be appreciated that there is also a stem cell stimulating and tissue regenerating effect that functions independent of the antimicrobial effects of the treatment.

For example, treatment of an infected tissue of a subject using a conventional antimicrobial, as compared to a CSA-based treatment composition, may provide comparable removal of the underlying infection, but with less recovery of tissue and/or less ability to withstand tissue atrophy. Disclosed treatment methods therefore provide effective stimulation of stem cells and promotion of tissue regeneration independent of any additional antimicrobial activity.

A subject to which the treatment composition is applied may be any animal having damaged tissue, experiencing tissue loss or atrophy, or at risk for tissue loss or atrophy. The tissue may be targeted because of injury, infection, a hereditary condition, atrophy or degeneration resulting from normal or premature aging, or risk thereof, for example.

In particular applications where the treatment compositions are directed to hair follicle tissue in order to stimulate hair growth, the subject may be any mammal experiencing or at risk of experiencing hair loss. Examples include pets, livestock, laboratory animals, zoo animals, and humans. The actual or potential hair loss may be associated with an infection (e.g., dermatophytosis or other dermal fungal infection), or may be associated with a hereditary condition, hormonal imbalance, burn, sun damage, or other injury to the dermal tissue, for example.

In embodiments, a CSA-based treatment composition is applied in a relatively short or temporary regimen until the targeted tissue has sufficiently regenerated or until the underlying cause(s) of tissue atrophy are no longer present. For example, where problems are associated with an underlying infection, a treatment composition may be applied until the underlying infection has cleared. In such circumstances, application of the CSA-based treatment composition may beneficially promote more rapid recovery of the tissue and/or provide more effective regeneration (e.g., thicker/fuller hair growth in a follicle/hair application) as compared to treating the underlying infection conventionally and waiting for or hoping for the tissue to recover as a matter of course.

In other embodiments, a CSA-based treatment composition is applied in a more continuous manner. For example, the treatment composition may be applied prophylactically to reverse or prevent tissue atrophy or degradation. In such circumstances, the treatment composition may be applied multiple times a day (e.g., morning and night), daily, weekly, or at a frequency suitable to provide sufficient tissue regeneration and maintenance. One example of such a use is to reverse and/or prevent hair loss where the subject has suffered hair loss or is at risk of hair loss.

In topical applications, the treatment composition may administered using a pharmaceutically acceptable carrier, such as a solvent, surfactant, skin-penetrating agent (e.g., ethanol, isopropyl alcohol, other alcohol, dimethyl sulfoxide), oil, emulsion, water, and/or combinations thereof. The composition may be provided in the form of a liniment, lotion, ointment, cream, powder, wash, or spray, for example. The composition may also be incorporated into another topically applied product, such as a shampoo, conditioner, soap, hair-care product, and the like. In other embodiments, the treatment composition may additionally or alternatively be using another non-topical administration route, such as through injection, oral ingestion, or inhalation.

In embodiments, the one or more CSA compounds are included by weight in the treatment composition at about 0.01%, 0.1%, 0.2%, 0.3%, 0.5%, 1%, 2%, 3%, 5%, 10%, 15%, 20%, 25%, or 30%, or are included by weight within a range defined by any two of the foregoing percentage values. Presently preferred ranges include one or more CSA compounds at about 0.1% to about 5%, or about 0.2% to about 3%, or about 0.3% to about 2%. In embodiments, the one or more CSA compounds are included at a concentration of about 1 µg/ml, 5 µg/ml, 10 µg/ml, 25 µg/ml, 50 µg/ml, 100 µg/ml, 150 µg/ml, or 200 µg/ml, or are included at a concentration within a range defined by any two of the foregoing concentration values.

It will be understood that in the foregoing examples, the upper concentration endpoints do not necessarily represent a lack of effectiveness at CSA concentrations beyond the upper endpoints. Rather, the upper range endpoints define ranges for which effective activity may be achieved without the need for additional CSA compounds, thereby providing efficient use of CSA compounds given the associated formulation costs. In some implementations, such as where costs are less important than providing greater activity, the one or more CSA compounds may be included at concentrations higher than the foregoing ranges.

In embodiments, treatment of a subject with a CSA-based treatment composition is able to stop or at least slow tissue degeneration. In embodiments, treatment of a subject with a CSA-based treatment composition is able to stimulate regeneration of tissue.

In embodiments, treatment of a subject with a CSA-based treatment composition is able to stop or at least slow hair loss. In embodiments, treatment of a subject with a CSA-based treatment composition is able to stimulate regeneration of hair growth. Treatment of a subject with a CSA-based treatment composition may promote hair growth at a rate that is about 1.2 to 5, or about 1.5 to 3 times the rate of hair regeneration with conventional treatment or without treatment.

Any CSA compound described herein, or any combination of such CSA compounds may be utilized in a treatment composition. In preferred embodiments, the treatment composition includes one or more CSA compounds having hydrolysable linkages. Exemplary CSA compounds include CSA-44, CSA-142, CSA-144, CSA-145, CSA-146, and CSA-148, in particular CSA-44, CSA-142, CSA-144, and CSA-148.

III. EXAMPLES

Example 1

A mouse model was used to test the effectiveness of a CSA-based treatment composition in stimulating stem cells and regenerating hair growth. Male C57BL/6 mice aged 8 weeks, were housed under environmentally monitored conditions and were fed a standard rodent diet. The hair on the dorsal surface of each mouse was shaved with an animal clipper, which was then followed by application of a depilatory cream to clean the remaining hair as described by Jung M K et al (Life Sci. 2015 May 1; 128:39-46). The mice were then allowed to rest for 24 h.

On the day of experiment, all the animals were weighed and randomized into different treatment groups (n=8) according to body weight. Randomized animals were identified by individual animal marking and cage cards were used for group identification.

The animals of Group 1, the control mice, were treated topically with the cream-based vehicle. The animals of Group 2 were treated topically with 100 mg of 0.5 CSA-44 once daily for 3 weeks. The animals in Group 3 were treated topically with 100 mg of 2.0% CSA-44 test compound once every other day for 3 weeks. The dose levels of test item and the respective treatment group details are provided in Table 1.

TABLE 1

Test Group Details

| Group | Description | Dose | Route of administration | Dose frequency | No. of animals |
|---|---|---|---|---|---|
| 1 | Vehicle Control | Vehicle | Topical | Once daily for 3 weeks | 8 |
| 2 | CSA-44 | 0.5% | Topical | Once daily for 3 weeks | 8 |
| 3 | CSA-44 | 2% | Topical | Once every other day for 3 weeks | 8 |

A preliminary tolerability study was conducted in C57BL/6 mice for selecting an appropriate well tolerated dose for the present efficacy study. Based on the results from the preliminary dose tolerability study, 100 mg of a formulation containing 0.5% CSA-44 was uniformly applied topically on the shaven areas of the dorsal skin once daily for 3 weeks. Similarly, 100 mg of 2% CSA-44 formulation was applied topically every other day for 3 weeks. 100 mg of cream vehicle was applied topically on the shaved areas once daily for 3 weeks.

Hair Growth Scoring

The hair-growth score was evaluated using the scoring pattern below as described by Vegesna et al (Endocrinology 143(11):4389-4396). A score of '0' indicates no change in the amount of hair growth compared with the hair-loss induction day and a score of '10' indicates full hair growth on the entire site on the dorsal skin. Darkening and hair-growth rate was monitored twice weekly for 3 weeks. Images of the dorsal skin of the mice were captured using a digital camera at weekly intervals to notice the start of hair regrowth period and the hair regrowth pattern.

TABLE 2

Scoring Criteria

| Score | Scoring pattern |
|---|---|
| 1 | Skin pink, no hair |
| 2 | Skin thick, pigmented, no hair |
| 3 | Skin thick, highly pigmented, no hair |
| 4 | Skin thick, pigmented, scattered hair |
| 5 | 1-10% of hair regrowth |
| 6 | 10-25% of hair regrowth |
| 7 | 25-50% of hair regrowth |
| 8 | 50-75% of hair regrowth |
| 9 | >75% of hair regrowth |
| 10 | 100% of hair regrowth |

Body weight of the animals were recorded once prior to randomization (pre dose) and twice weekly during the course of the study. All animals were observed once daily for clinical signs and twice daily (morning and evening) for mortality and morbidity. No mortality was observed during the study period. Animals were sacrificed at the end of the study period by following a standard protocol using $CO_2$ induced euthanasia. Results Hair growth score and body weight were recorded twice weekly during the study period. The percentage (%) change in hair growth was calculated on Day 21 by comparing the treated mice with the vehicle treated control group.

Effect of CSA-44: Animals treated with 0.5% of CSA-44 showed a significant ($p<0.05$) 72% increase in hair growth compared to the vehicle treated animals. At the end of 3-weeks of application, the mice exhibited an average hair growth score of 6.88 compared to the control group which exhibited a score of 4.

Animals treated with the cream containing 2% CSA-44 showed a significant (p<0.05) 66% increase in hair growth compared to the vehicle treated group. At the end of 3-weeks of application, the animals reached an average hair growth score of 6.63 while the vehicle control group exhibited an average score of 4.

TABLE 3

Hair Growth Scores (Represented as Mean ± SE, n = 8)

| No. | Treatment groups | Dose | Day 1 | Day 3 | Day 7 | Day 10 | Day 14 | Day 17 | Day 21 | Percentage Change in Hair growth |
|---|---|---|---|---|---|---|---|---|---|---|
| 1 | Vehicle Control | Vehicle | 0.00 ± 0.0 | 0.25 ± 0.2 | 0.25 ± 0.2 | 0.50 ± 0.2 | 1.13 ± 0.3 | 2.63 ± 0.3 | 4.00 ± 0.6 | — |
| 2 | CSA-44 | 0.5% | 0.00 ± 0.0 | 0.25 ± 0.2 | 0.50 ± 0.2 | 1.38 ± 0.3 | 2.63 ± 0.4 | 4.88 ± 0.9 | 6.88 ± 0.9* | 72 |
| 3 | CSA-44 | 2% | 0.00 ± 0.0 | 0.38 ± 0.2 | 0.50 ± 0.2 | 1.50 ± 0.2 | 2.50 ± 0.4 | 4.13 ± 0.6 | 6.63 ± 0.7* | 66 |

*P < 0.005, ***P < 0.0001, One-way ANOVA followed by Dunnett's test compared to Control.

Figure 2A:
FIGS. 2A through 2C are photographs showing hair growth in mice in a control group and two CSA treatment groups at 7, 14, and 21 days following hair removal, respectively.
Figure 2A:
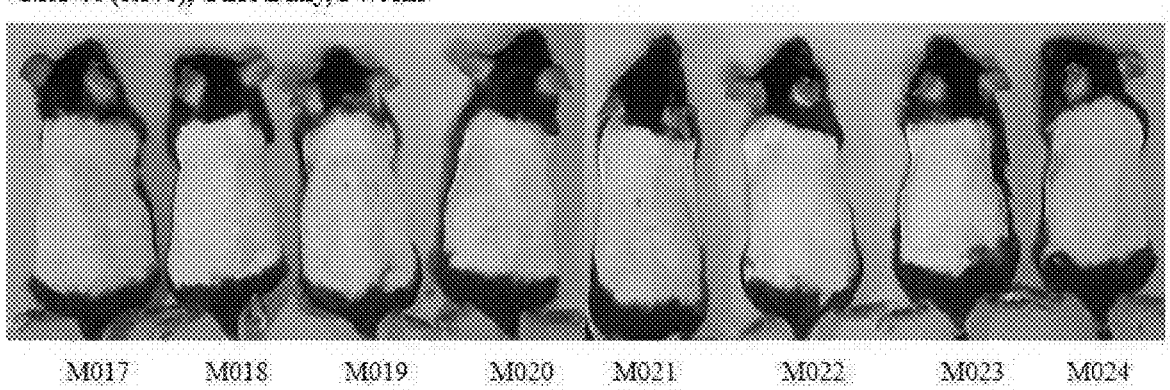
Figure 2A:
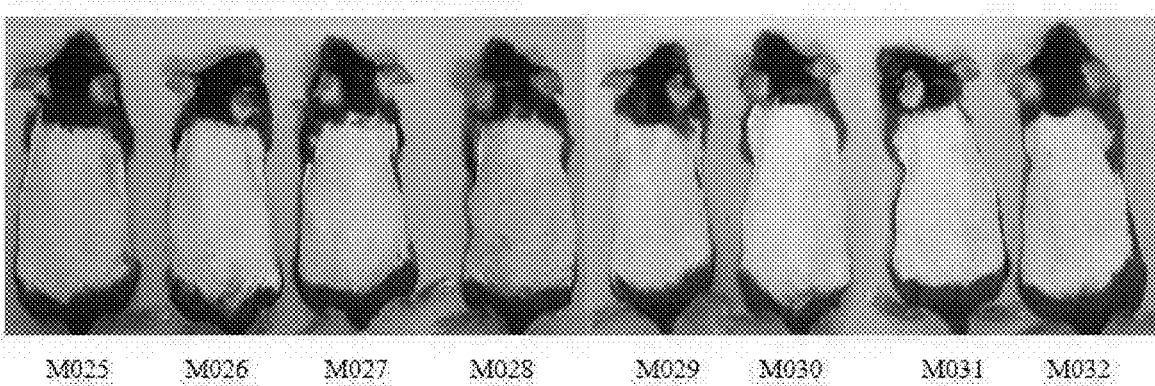
Figure 2B:
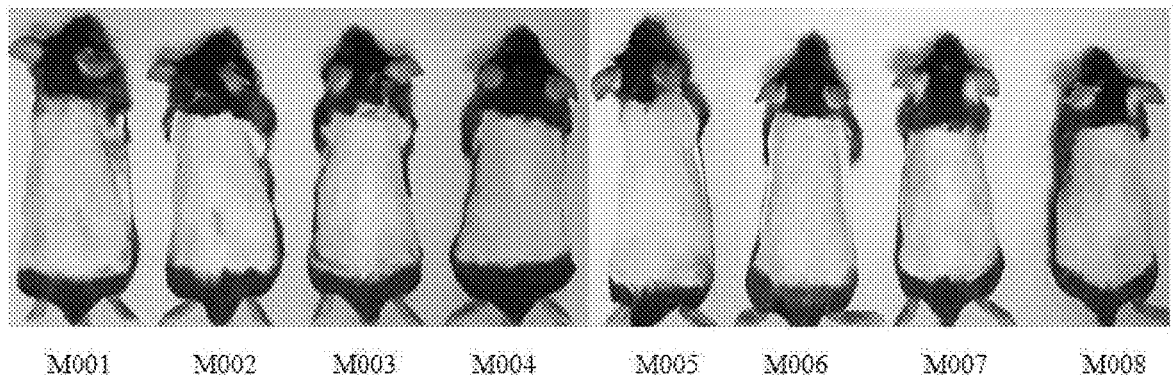
Figure 2B:
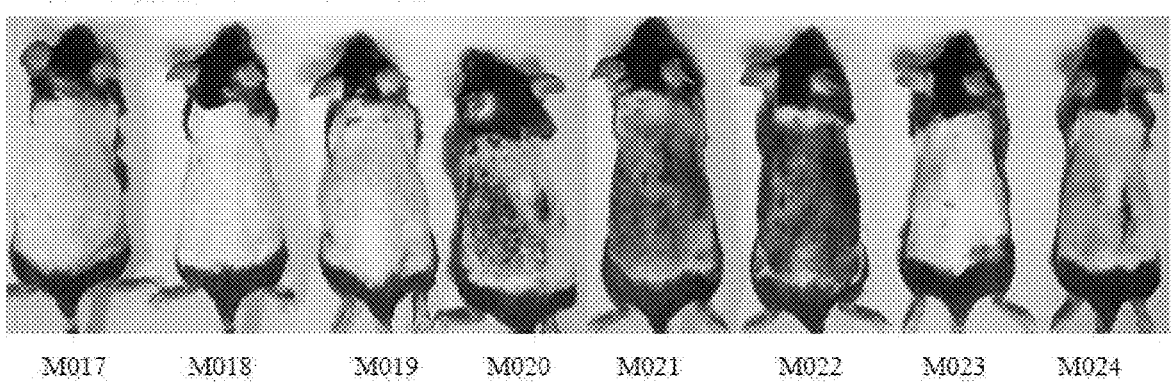
Figure 2B:
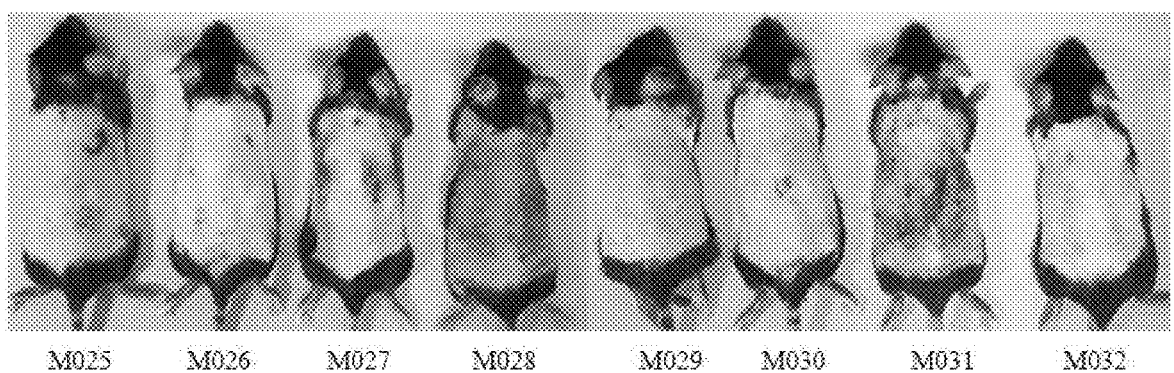
Figure 2C:
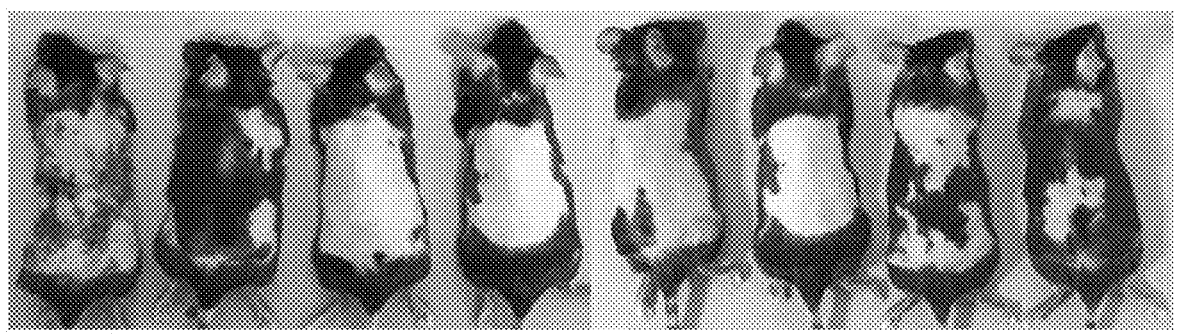
Figure 2C:
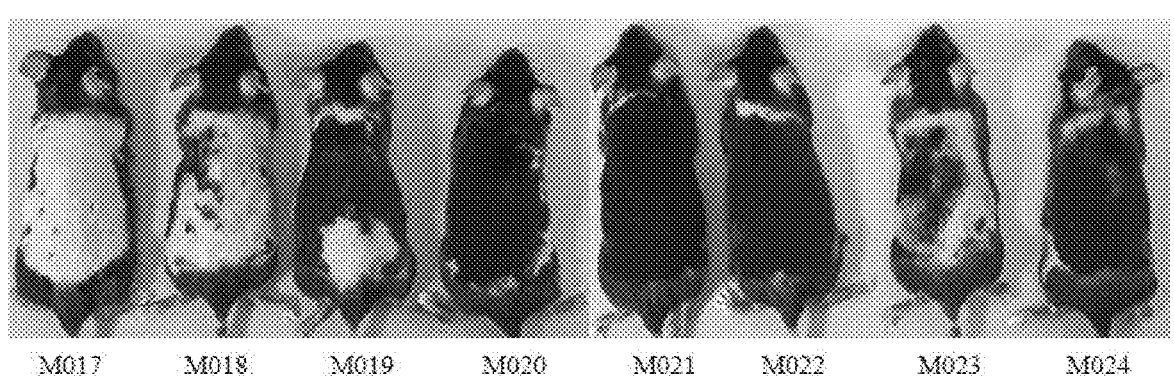
Figure 2C:
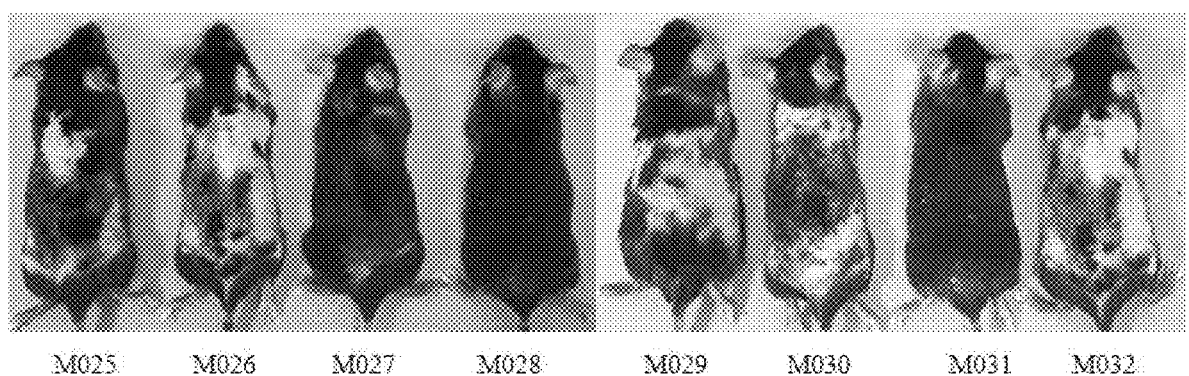
Figure 3A:
FIGS. 3A and 3B are photographs showing a horse suffering hair loss before and after, respectively, treatment with a CSA-based treatment composition.
Figure 3A:
Figure 3B:

The skin areas with black hair in the CSA-44 treated group were larger than that of the control group. At the end of 2 weeks, many new hairs from hair follicles were observed on the depilated back skin accompanied by a change in skin color to dark gray. Growth of hair was seen partially while some parts of the skin was still pink. At the end of 3 weeks, the skin area with black hair in the CSA-44 treated groups were larger than that in the control group. Photographs showing hair growth progression are shown in FIGS. 2A through 2C. FIG. 2A shows hair growth at 7 days post removal, FIG. 2B shows hair growth at 14 days post removal, and FIG. 2C shows hair growth at 21 days post removal.

Example 2

A treatment composition including CSA-44 was applied to a horse having a "summer itch" condition associated with a dermal fungal infection. FIG. 2A shows photographs of the subject horse prior to treatment. As shown, the subject horse had several patches of visible hair loss. FIG. 2B shows a photograph of the subject horse after 18 days of treatment. As shown, hair had regrown to completely fill in the previous patches and the regrown hair was thick and full. Typical time for hair to grow back on a horse following treatment of such a fungal infection is approximately 28 days. The CSA-based treatment therefore regenerated hair growth 1.56 times faster than a conventional treatment.

Example 3

A CSA-based treatment composition including one or more of CSA-44, CSA-142, CSA-144, CSA-145, CSA-146, or CSA-148 is applied to a dermatophyte-infected dermal area of a first mammal subject. A conventional antifungal composition containing clotrimazole is applied to a dermatophyte-infected dermal area of a second mammal subject. A conventional antifungal composition containing tioconazole is applied to a dermatophyte-infected dermal area of a third mammal subject. A conventional antifungal composition containing tolnaftate is applied to a dermatophyte-infected dermal area of a fourth mammal subject. A conventional antifungal composition containing terbinafine is applied to a dermatophyte-infected dermal area of a fifth mammal subject. A conventional antifungal composition containing miconazole is applied to a dermatophyte-infected dermal area of a sixth mammal subject. A conventional antifungal composition containing nystatin is applied to a dermatophyte-infected dermal area of a seventh mammal subject. A conventional antifungal composition containing butenafine is applied to a dermatophyte-infected dermal area of an eighth mammal subject. A conventional antifungal composition containing fluconazole is applied to a dermatophyte-infected dermal area of a ninth mammal subject. A conventional antifungal composition containing terconazole is applied to a dermatophyte-infected dermal area of a tenth mammal subject.

The dermatophyte-infections of all subjects are seen to clear. Hair growth is seen to return to the affected areas of the first subject about 1.5 to 5 times faster than to the affected areas of the second through tenth subjects.

Example 4

A CSA composition including one or more of CSA-44, CSA-142, CSA-144, CSA-145, CSA-146, or CSA-148 is applied daily to the scalp of a human male experiencing early stage hair loss. Hair loss is seen to stop after about 1 to 10 days of treatment. Hair regeneration is seen to begin after about 5 to 30 days of treatment.

IV. ADDITIONAL DETAILS OF CSA COMPOUNDS

Exemplary CSA compounds and methods for their manufacture are described in U.S. Pat. Nos. 6,350,738, 6,486,148, 6,767,904, 7,598,234, 7,754,705, 8,691,252, 8,975,310, 9,434,759, 9,527,883, 9,943,614, 10,155,788, 10,227,376, 10,370,403, and 10,626,139, U.S. Pat. Pub. Nos. 2016/0311850 and 2017/0210776, and U.S. Prov. Pat. App. Nos. 63/025,255 and 63/028,249, which are incorporated herein by reference. The skilled artisan will recognize the compounds within the generic formulae set forth herein and understand their preparation in view of the references cited herein and the Examples.

CSA compounds can have a structure of Formula I, Formula II, Formula III, and/or Formula IV. Formula III differs from Formula I and II by omitting $R_{15}$ and the ring carbon to which it is attached. Formula IV more particularly defines Formula III with respect to stereochemistry and R groups for all but $R_3$, $R_7$, $R_{12}$, and $R_{18}$.

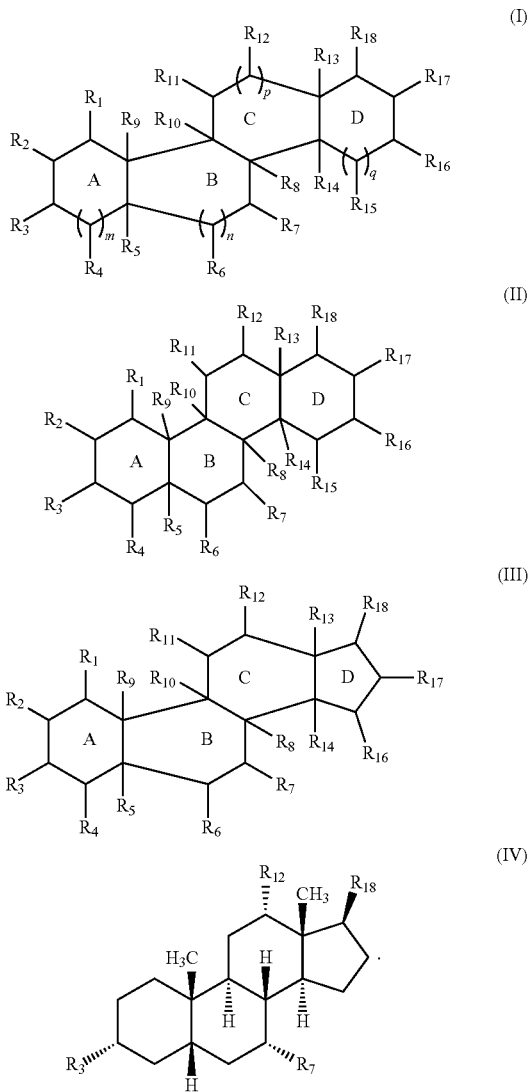

In embodiments of Formulas I, II, III, and IV, at least two of $R_3$, $R_7$, and $R_{12}$ may independently include a cationic moiety (e.g., amino or guanidino groups) bonded to the steroid backbone structure via a hydrolysable or non-hydrolysable linkage. For the embodiments of the present disclosure, the linkage is preferably hydrolysable but stable under conditions of sterilization and storage, and hydrolysable under physiological conditions. Such cationic functional groups (e.g., amino or guanidino groups) may be separated from the backbone by at least one, two, three, four or more atoms.

A tail moiety may be attached to the sterol backbone at $R_{18}$, may have variable chain length or size, and may be charged, uncharged, polar, non-polar, hydrophobic, or amphipathic. The tail moiety may be used to select the hydrophobicity/hydrophilicity of the ceragenin compound. CSA compounds having different degrees of hydrophobicity/hydrophilicity may have different rates of uptake into different target microbes.

The "R" groups described herein, unless specified otherwise, may be substituted or unsubstituted.

With respect to CSA compounds of Formulas I, II, and III (and where not already specified with respect to Formula IV):

each of fused rings A, B, C, and D may be independently saturated, or may be fully or partially unsaturated, provided that at least two of A, B, C, and D is saturated, wherein rings A, B, C, and D form a ring system. Other ring systems can also be used, e.g., 5-member fused rings and/or compounds with backbones having a combination of 5- and 6-membered rings;

$R_1$ through $R_{18}$ are independently selected from the group consisting of hydrogen, hydroxyl, alkyl, hydroxyalkyl, alkyloxyalkyl, alkylcarboxyalkyl, terpenylcarboxyalkyl, terpenylcarbonyloxyalkyl, terpenylamidoalkyl, terpenylaminoalkyl, terpenyloxyalkyl, alkylaminoalkyl, alkylaminoalkylamino, alkylaminoalkylaminoalkylamino, aminoalkyl, aryl, arylaminoalkyl, haloalkyl, alkenyl, alkynyl, oxo, linking group attached to a second steroid, aminoalkylurethanyl, aminoalkenylurethanyl, aminoalkynylurethanyl, aminoarylurethanyl, aminoalkyloxy, aminoalkylcarboxy, aminoalkyloxyalkyl, aminoalkylaminocarbonyl, aminoalkylcarboxamido, di(alkyl)aminoalkyl, $H_2N-HC(Q_5)-(C=O)-O-$, $H_2N-HC(Q_5)-(C=O)-NH-$, azidoalkyloxy, cyanoalkyloxy, P.G.-HN-HC(Q_5)-(C=O)-O-, guanidinoalkyloxy, quaternary ammonium alkylcarboxy, and guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, provided that at least one, and sometimes two, three, or four, of $R_{1-4}$, $R_6$, $R_7$, $R_{11}$, $R_{12}$, $R_{15}$, $R_{16}$, $R_{17}$, and $R_{18}$ are independently selected from the group consisting of aminoalkyl, aminoalkyloxy, aminoalkylcarboxyalkyl, alkylaminoalkyl, alkylamino-alkylamino, alkylaminoalkylaminoalkylamino, aminoalkylcarboxy, aryl-aminoalkyl, aminoalkyloxyamino, alkylaminocarbonyl, aminoalkylaminocarbonyl, aminoalkyl-carboxamido, di(alkyl)aminoalkyl, aminoalkylurethanyl, aminoalkenyl-urethanyl, aminoalkynylurethanyl, aminoarylurethanyl, $H_2N-HC(Q_5)-C(O)-O-$, $H_2N-HC(Q_5)-C(O)-N(H)-$, azidoalkyloxy, cyanoalkyloxy, P.G.-HN-HC(Q_5)-C(O)-O-, guanidinoalkyloxy, quaternary ammonium alkylcarboxy, and guanidinoalkylcarboxy.

In embodiments, Ri through $R_4$, $R_6$, $R_7$, $R_{11}$, $R_{12}$, $R_{15}$, $R_{16}$, and $R_{18}$ are independently selected from the group consisting of hydrogen, hydroxyl, substituted or unsubstituted $(C_1-C_{22})$alkyl, substituted or unsubstituted $(C_1-C_{22})$hydroxyalkyl, substituted or unsubstituted $(C_1-C_{22})$alkyloxy-$(C_1-C_{22})$alkyl, substituted or unsubstituted $(C_1-C_{22})$alkylcarboxy-$(C_1-C_{22})$alkyl, substituted or unsubstituted $(C_5-C_{25})$terpenyl-carboxy-$(C_1-C_{22})$alkyl, substituted or unsubstituted $(C_5-C_{25})$terpenylcarbonyloxy-$(C_1-C_{22})$alkyl, substituted or unsubstituted $(C_5-C_{25})$terpenylcarboxamido-$(C_1-C_{22})$alkyl, substituted or unsubstituted $(C_5-C_{25})$terpenylamino-$(C_1-C_{22})$alkyl, $(C_5-C_{25})$terpenyloxyo-$(C_1-C_{22})$alkyl, substituted or unsubstituted $(C_1-C_{22})$alkylamino-$(C_1-C_{22})$alkyl, substituted or unsubstituted $(C_1-C_{22})$alkylamino-$(C_1-C_{22})$alkylamino, substituted or unsubstituted $(C_1-C_{22})$alkylamino-$(C_1-C_{22})$alkylamino-$(C_1-C_{22})$alkylamino, substituted or unsubstituted $(C_1-C_{22})$aminoalkyl, substituted or unsubstituted aryl, substituted or unsubstituted arylamino-$(C_1-C_{22})$alkyl, substituted or unsubstituted $(C_1-C_{22})$haloalkyl, substituted or unsubstituted $(C_2-C_6)$alkenyl, substituted or unsubstituted $(C_2-C_6)$alkynyl, oxo, linking group attached to a second steroid, substituted or unsubstituted $(C_1-C_{22})$aminoalkylurethanyl, substituted or unsubstituted $(C_2-C_{22})$aminoalkenylurethanyl, substituted or unsubstituted $(C_2-C_{22})$aminoalkynylurethanyl, and substituted or unsubstituted aminoarylurethanyl, substituted or unsubstituted $(C_1-C_{22})$aminoalkyloxy, substituted or unsubstituted $(C_1-C_{22})$aminoalkylcarboxy, substituted or unsubstituted $(C_1-C_{22})$aminoalkyloxy-$(C_1-C_{22})$alkyl, substituted or unsubstituted $(C_1-C_{22})$aminoalkyl-aminocarbonyl, substituted or unsubstituted $(C_1-C_{22})$aminoalkylcarboxamido, substituted or unsubstituted di$(C_1-C_{22})$alkylamino-$(C_1-C_{22})$ alkyl, $H_2N-HC(Q_5)-(C=O)-O-$, $H_2N-HC(Q_5)-(C=O)-NH-$, substituted or unsubstituted $(C_1-C_{22})$azidoalkyloxy, substituted or unsubstituted $(C_1-C_{22})$ cyanoalkyloxy, P. G.-HN—HC$(Q_5)$-(C=O)—O—, substituted or unsubstituted $(C_1-C_{22})$guanidinoalkyloxy, substituted or unsubstituted quaternary ammonium $(C_1-C_{22})$ alkylcarboxy, and substituted or unsubstituted $(C_1-C_{22})$guanidinoalkyl carboxy, where $Q_5$ is a side chain of an amino acid (including a side chain of glycine, i.e., H), and P.G. is an amino protecting group; and $R_5$, Rs, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, $(C_1-C_{22})$alkyl, $(C_1-C_{22})$hydroxyalkyl, $(C_1-C_{22})$alkyloxy-$(C_1-C_{22})$alkyl, $(C_1-C_{22})$ aminoalkyl, aryl, $(C_1-C_{22})$haloalkyl, $(C_2-C_6)$alkenyl, $(C_2-C_6)$alkynyl, oxo, a linking group attached to a second steroid, $(C_1-C_{22})$aminoalkyloxy, $(C_1-C_{22})$aminoalkylcarboxy, $(C_1-C_{22})$aminoalkylaminocarbonyl, di$(C_1-C_{22}$ alkyl)amino-$(C_1-C_{22})$alkyl, $H_2N-HC(Q_5)-C(O)-O-$, $H_2N-HC(Q_5)-C(O)-N(H)-$, $(C_1-C_{22})$ azidoalkyloxy, $(C_1-C_{22})$ cyanoalkyloxy, P.G.-HN-HC$(Q_5)$-C(O)—O—, $(C_1-C_{22})$ guanidinoalkyloxy, and $(C_1-C_{22})$ guanidinoalkylcarboxy, where $Q_5$ is a side chain of an amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of $(C_1-C_{22})$aminoalkyl, $(C_1-C_{22})$aminoalkyloxy, $(C_1-C_{22})$alkylcarboxy-$(C_1-C_{22})$alkyl, $(C_1-C_{22})$ alkylamino-$(C_1-C_{22})$alkylamino, $(C_1-C_{22})$alkylamino-$(C_1-C_{22})$alkylamino-$(C_1-C_{22})$alkylamino, $(C_1-C_{22})$ aminoalkylcarboxy, arylamino-$(C_1-C_{22})$alkyl, $(C_1-C_{22})$ aminoalkyloxy $(C_1-C_{22})$aminoalkylaminocarbonyl, $(C_1-C_{22})$aminoalkylaminocarbonyl, $(C_1-C_{22})$aminoalkylcarboxyamido, quaternary ammonium $(C_1-C_{22})$ alkylcarboxy, di$(C_1-C_{22}$ alkyl)amino-$(C_1-C_{22})$alkyl, $(C_1-C_{22})$aminoalkylurethanyl, $(C_2-C_{22})$aminoalkenylurethanyl, $(C_2-C_{22})$amino-alkynylurethanyl, aminoarylurethanyl, $H_2N-HC(Q_5)-C(O)-O-$, $H_2N-HC(Q_5)-C(O)-N(H)-$, $(C_1-C_{22})$ azidoalkyloxy, $(C_1-C_{22})$ cyanoalkyloxy, P.G.-HN—HC$(Q_5)$-C(O)—O—, $(C_1-C_{22})$ guanidinoalkyloxy, and $(C_1-C_{22})$ guanidinoalkylcarboxy.

In embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In embodiments, $R_1$, $R_2$, $R_4$, $R_5$, $R_6$, $R_8$, $R_{10}$, $R_{11}$, $R_{14}$, $R_{16}$, and $R_{17}$ are each hydrogen and $R_9$ and $R_{13}$ are each methyl.

In embodiments, $R_3$, $R_7$, $R_{12}$, and $R_{18}$ are independently selected from the group consisting of hydrogen, $(C_1-C_6)$ alkyl, $(C_1-C_6)$hydroxyalkyl, $(C_1-C_{16})$alkyloxy-$(C_1-C_5)$alkyl, $(C_1-C_{16})$alkylcarboxy-$(C_1-C_5)$alkyl, $(C_1-C_{16})$alkylamino-$(C_1-C_5)$alkyl, $(C_1-C_{16})$alkylamino-$(C_1-C_5)$alkylamino, $(C_1-C_{16})$alkylamino-$(C_1-C_{16})$alkylamino-$(C_1-C_5)$alkylamino, $(C_5-C_{25})$terpenylcarboxy-$(C_1-C_5)$alkyl, $(C_5-C_{25})$terpenylcarbonyloxy-$(C_1-C_5)$alkyl, $(C_5-C_{25})$ terpenylcarboxamido-$(C_1-C_5)$alkyl, $(C_5-C_{25})$terpenylamino-$(C_1-C_5)$alkyl, $(C_5-C_{25})$terpenyloxyo-$(C_1-C_5)$alkyl, $(C_1-C_6)$ aminoalkylurethanyl, $(C_2-C_6)$aminoalkenylurethanyl, $(C_2-C_6)$aminoalkynylurethanyl, aminoarylurethanyl, $(C_1-C_{16})$ aminoalkyl, arylamino-$(C_1-C_5)$alkyl, $(C_1-C_5)$ aminoalkyloxy, $(C_1-C_{16})$aminoalkyl-oxy-$(C_1-C_5)$alkyl, $(C_1-C_5)$aminoalkylcarboxy, $(C_1-C_5)$aminoalkyl-aminocarbonyl, $(C_1-C_5)$aminoalkylcarbox-amido, di$(C_1-C_5$ alkyl)amino-$(C_1-C_5)$alkyl, $(C_1-C_5)$guanidino-alkyloxy, quaternary ammonium $(C_1-C_{16})$alkylcarboxy, and unsubstituted $(C_1-C_{16})$ guanidinoalkylcarboxy.

In embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In embodiments, $R_3$, $R_7$, $R_{12}$, and $R_{18}$ are independently selected from the group consisting of aminoalkyloxy, aminoalkylcarboxy, alkylaminoalkyl, alkoxycarbonylalkyl, alkylcarbonylalkyl, di(alkyl)aminoalkyl, alkylcarboxyalkyl, hydroxyalkyl, terpenyl-carboxyalkyl, terpenylcarbonyloxyalkyl, terpenylcarboxamidoalkyl, terpenylamino-alkyl, terpenyloxyalkyl, aminoalkylurethanyl, aminoalkenylurethanyl, aminoalkynyl-urethanyl, and aminoarylurethanyl.

In embodiments, $R_3$, $R_7$, and $R_{12}$ are independently selected from the group consisting of aminoalkyloxy, aminoalkylcarboxy, aminoalkylurethanyl, aminoalkenyl-urethanyl, aminoalkynylurethanyl, and aminoarylurethanyl.

In embodiments, $R_{18}$ is selected from the group consisting of alkylaminoalkyl, alkoxycarbonylalkyl, alkylcarbonyloxyalkyl, alkylcarbonylalkyl, di(alkyl)aminoalkyl, alkylcarboxyalkyl, hydroxyalkyl, terpenylcarboxyalkyl, terpenylcarbonyloxyalkyl, terpenylcarboxamido-alkyl, terpenylaminoalkyl, and terpenyloxyalkyl.

In embodiments, one or more of rings A, B, C, and D is heterocyclic.

In embodiments, rings A, B, C, and D are non-heterocyclic.

The compounds and compositions disclosed herein are optionally prepared as salts, which advantageously makes them cationic when one or more amine groups is/are protonated. "Salt" as used herein is a broad term, and is to be given its ordinary and customary meaning to a skilled artisan (and is not to be limited to a special or customized meaning), and refers without limitation to a salt of a compound. In embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, phosphoric acid, and phosphonic acid. Salts can also be obtained by reacting a compound with an organic acid such as aliphatic or aromatic carboxylic or sulfonic acids, sulfinic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or 1,5-naphthalenedisulfonic acid (NDSA). Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1-C_7$ alkylamine, cyclohexyl-amine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In embodiments, the salt is a hydrochloride salt. In embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

"R" groups such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$, represent substituents that can be attached to the sterol backbone. Unless otherwise specified, an R group may be substituted or unsubstituted.

A "ring" can be heterocyclic or carbocyclic. "Saturated" means a ring in which each atom is either hydrogenated or substituted such that the valency of each atom is filled. "Unsaturated" means a ring where the valency of each atom of the ring may not be filled with hydrogen or other substituents. For example, adjacent carbon atoms in a fused ring can be double bound to each other. Unsaturation can also include deleting at least one of the following pairs and completing the valency of the ring carbon atoms at these deleted positions with a double bond, such as $R_5$ and $R_9$; $R_8$ and $R_{10}$; and $R_{13}$ and $R_{14}$.

Where a group is "substituted" it may be substituted with one, two, three or more of the indicated substituents, which may be the same or different, each replacing a hydrogen atom. If no substituents are indicated, the indicated "substituted" group may be substituted with one or more groups individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_mO—$, $R_b(CH_2)_nO—$, $R_cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group. A group that is not specifically labeled as substituted or unsubstituted may be considered to be either substituted or unsubstituted.

The terms "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$, $(CH_3)_2CHCH_2—$ and $(CH_3)_3C—$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

"Alkyl" means a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

"Alkenyl" means an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2, 3, or 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

"Alkynyl" means an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2, 3, or 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

"Aryl" means a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

"Aralkyl" and "aryl(alkyl)" mean an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc. , up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" mean a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

"Cycloalkyl" means a completely saturated (no double or triple bonds) mono- or multi- cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

"Cycloalkenyl" means a mono- or multi- cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

"Cycloalkynyl" means a mono- or multi- cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

"Alkoxy" or "alkyloxy" mean the formula —OR wherein R is an alkyl, an alkenyl, an alkynyl, a cycloalkyl, a cycloalkenyl or a cycloalkynyl as defined above. Examples of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

"Acyl" means a hydrogen, alkyl, alkenyl, alkynyl, aryl, or heteroaryl connected, as substituents, via a carbonyl group, such as —(C=O)—R. Examples include formyl, acetyl, propanoyl, benzoyl, and acryl. An acyl may be substituted or unsubstituted.

"Alkoxyalkyl" or "alkyloxyalkyl" mean an alkoxy group connected, as a substituent, via a lower alkylene group. Examples include alkyl-O-alkyl- and alkoxy-alkyl- with the terms alkyl and alkoxy defined herein.

"Hydroxyalkyl" means an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

"Haloalkyl" means an alkyl group in which one or more of the hydrogen atoms are replaced by a halogen (e.g., mono-haloalkyl, di-haloalkyl and tri-haloalkyl). Examples include chloromethyl, fluoromethyl, difluoromethyl, trifluoromethyl and 1-chloro-2-fluoromethyl, 2-fluoroisobutyl. A haloalkyl may be substituted or unsubstituted.

"Amino" means "—$NH_2$".
"Hydroxy" means "—OH".
"Cyano" means "—CN".
"Carbonyl" or "oxo" mean "-C=O".
"Azido" means "—$N_3$".

"Aminoalkyl" means an amino group connected, as a substituent, via a lower alkylene group. Examples include $H_2$N-alkyl- with the term alkyl defined herein.

"Alkylcarboxyalkyl" means an alkyl group connected, as a substituent, to a carboxy group that is connected, as a substituent, to an alkyl group. Examples include alkyl-(C=O)—O-alkyl- and alkyl-O—(C=O)-alkyl- with the term alkyl as defined herein.

"Alkylaminoalkyl" means an alkyl group connected, as a substituent, to an amino group that is connected, as a substituent, to an alkyl group. Examples include alkyl-NH-alkyl- with the term alkyl as defined herein.

"Dialkylaminoalkyl" and "di(alkyl)aminoalkyl" mean two alkyl groups connected, each as a substituent, to an amino group that is connected, as a substituent, to an alkyl group. Examples include

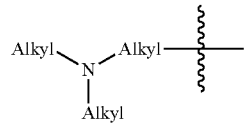

with the term alkyl as defined herein.

"Alkylaminoalkylamino" means an alkyl group connected, as a substituent, to an amino group that is connected, as a substituent, to an alkyl group that is connected, as a substituent, to an amino group. Examples include alkyl-NH-alkyl-NH— with the term alkyl as defined herein.

"Alkylaminoalkylaminoalkylamino" means an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl- with the term alkyl as defined herein.

"Arylaminoalkyl" means an aryl group connected, as a substituent, to an amino group that is connected, as a substituent, to an alkyl group. Examples include aryl-NH-alkyl- with the terms aryl and alkyl as defined herein.

"Aminoalkyloxy" means an amino group connected, as a substituent, to an alkyloxy group. Examples include $H_2$N-alkyl-O- and $H_2$N-alkoxy- with the terms alkyl and alkoxy as defined herein.

"Aminoalkyloxyalkyl" means an amino group connected, as a substituent, to an alkyloxy group connected, as a substituent, to an alkyl group. Examples include $H_2$N-alkyl-O-alkyl- and $H_2$N-alkoxy-alkyl- with the terms alkyl and alkoxy as defined herein.

"Aminoalkylcarboxy" means an amino group connected, as a substituent, to an alkyl group connected, as a substituent, to a carboxy group. Examples include H$_2$N-alkyl-(C═O)—O— and H$_2$N-alkyl-O—(C═O)— with the term alkyl as defined herein.

"Aminoalkylaminocarbonyl" means an amino group connected, as a substituent, to an alkyl group connected, as a substituent, to an amino group connected, as a substituent, to a carbonyl group. Examples include H$_2$N-alkyl-NH—(C═O)— with the term alkyl as defined herein.

"Aminoalkylcarboxamido" means an amino group connected, as a substituent, to an alkyl group connected, as a substituent, to a carbonyl group connected, as a substituent to an amino group. Examples include H$_2$N-alkyl-(C═O)—NH— and H$_2$N-alkyl-NH—(C═O)— with the term alkyl as defined herein.

"Azidoalkyloxy" means an azido group connected as a substituent, to an alkyloxy group. Examples include N$_3$-alkyl-O— and N$_3$-alkoxy- with the terms alkyl and alkoxy as defined herein.

"Cyanoalkyloxy" means a cyano group connected as a substituent, to an alkyloxy group. Examples include NC-alkyl-O— and NC-alkoxy- with the terms alkyl and alkoxy as defined herein.

"Sulfenyl" means "—SR" in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

"Sulfinyl" means "—(S═O)—R" in which R can be the same as defined with respect to sulfenyl. A sulfinyl may be substituted or unsubstituted.

"Sulfonyl" means "—(S═O)—OR" in which R can be the same as defined with respect to sulfenyl. A sulfonyl may be substituted or unsubstituted.

"O-carboxy" means "R—(C═O)—O—" in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

"Ester" and "C-carboxy" mean "—(C═O)—OR" in which R can be the same as defined with respect to O-carboxy. An ester and C-carboxy may be substituted or unsubstituted.

"Thiocarbonyl" means "—(C═S)—R" in which R can be the same as defined with respect to O-carboxy. A thiocarbonyl may be substituted or unsubstituted.

"Trihalomethanesulfonyl" means "X$_3$CSO$_2$—" wherein X is a halogen.

"S-sulfonamido" means "—SO$_2$N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

"N-sulfonamido" means "RSO$_2$N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

"0-carbamyl" and "urethanyl" mean "—O—(C═O)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl or urethanyl may be substituted or unsubstituted.

"N-carbamyl" means "RO—(C═O)—N(RA)—" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

"0-thiocarbamyl" means "—O—(C═S)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

"N-thiocarbamyl" means "RO—(C═S)—N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

C-amido" means "—(C═O)—N(RARB)" in which RA and RB are independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

"N-amido" means "R—(C═O)—N(RA)-" in which R and RA are independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

"Guanidinoalkyloxy" means a guanidinyl group connected, as a substituent, to an alkyloxy group. Examples are

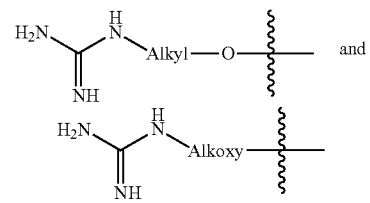

with the terms alkyl and alkoxy as defined herein.

"Guanidinoalkylcarboxy" means a guanidinyl group connected, as a substituent, to an alkyl group connected, as a substituent, to a carboxy group. Examples are

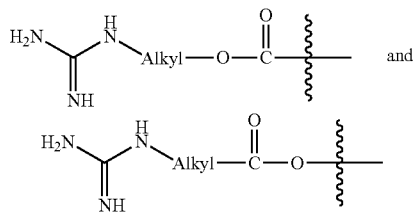

with the term alkyl as defined herein.

"Quaternary ammonium alkylcarboxy" means a quaternized amino group connected, as a substituent, to an alkyl group connected, as a substituent, to a carboxy group. Examples are

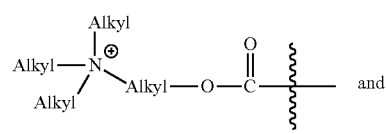

-continued

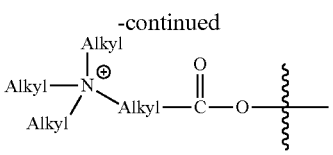

with the term alkyl as defined herein.

"Halogen atom" and "halogen" mean any one of the radio-stable atoms of column 7 of the Periodic Table of the Elements, such as, fluorine, chlorine, bromine and iodine.

Where the number of substituents is not specified (e.g. haloalkyl), there may be one or more substituents present. For example, "haloalkyl" may include one or more of the same or different halogens.

"Amino acid" means any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, γ-aminobutyric acid, citrulline, β-alanine, α-ethyl-glycine, α-propyl-glycine and norleucine.

A "linking group" is a divalent moiety used to link one steroid to another steroid. In embodiments, the linking group is used to link a first CSA with a second CSA (which may be the same or different). An example of a linking group is $(C_1-C_{10})$ alkyloxy-$(C_1-C_{10})$ alkyl.

"P.G." or "protecting group" or "protecting groups" mean any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of regenerating tissue and/or preventing tissue atrophy, the method comprising:
   providing a treatment composition including one or more cationic steroidal antimicrobial (CSA) compounds in a carrier;
   directly applying the treatment composition to targeted tissue of a subject that is in need of regeneration and is not infected with a microbial infection or associated with a dermal tissue wound; and
   the one or more CSA compounds stimulating tissue-specific stem cells to proliferate and promote tissue regeneration and/or prevent tissue atrophy at the targeted tissue to which it is applied, wherein the tissue-specific stem cells are selected from the group consisting of follicular stem cells, hematopoietic stem cells, neural stem cells, and stem cells found in one or more of peripheral blood, brain, spinal cord, dental pulp, blood vessels, skeletal muscle, hair follicle tissue, epithelia of the digestive system, cornea, retina, liver, or pancreas; wherein the targeted tissue is tissue damaged as a result of stroke, an autoimmune disease, a brain injury, or a cardiac injury or disorder.

2. The method of claim 1, wherein the treatment composition includes one or more CSA compounds having hydrolysable linkages.

3. The method of claim 2, wherein a majority, by weight, of the CSA compounds included in the treatment composition are CSA compounds having hydrolysable linkages.

4. The method of claim 3, wherein all of the CSA compounds included in the treatment composition are CSA compounds having hydrolysable linkages.

5. The method of claim 2, wherein the hydrolysable linkages are ester linkages.

6. The method of claim 1, wherein the one or more CSA compounds include one or more of CSA-44, CSA-142, CSA-144, CSA-145, CSA-146, and CSA-148.

7. The method of claim 1, wherein the treatment composition is applied to a dermal region that is not infected with a microbial infection or associated with a dermal tissue wound, and wherein the treatment composition regenerates hair follicles to thereby stimulate hair growth and/or prevent hair loss.

8. The method of claim 1, wherein the subject is a human, livestock animal, pet, laboratory animal, or zoo animal.

9. The method of claim 7, wherein the dermal region is affected by hair loss or is at risk of being affected by hair loss as a result of one or more of hereditary condition or hormonal imbalance, or injury other than a dermal tissue wound.

10. The method of claim 7, wherein the subject is a human and the dermal region is the scalp.

11. The method of claim 1, wherein the carrier is selected from the group consisting of water, alcohol, dimethyl sulfoxide, organic solvent, emulsion, and combinations thereof.

12. The method of claim 1, wherein the treatment composition is provided in the form of a liniment, lotion, ointment, cream, powder, wash, or spray.

13. The method of claim 1, wherein the treatment composition is incorporated into a shampoo, conditioner, or hair-care product.

14. The method of claim 7, wherein the treatment composition regenerates hair growth at about 1.2 to 5 times or about 1.5 to 3 times the rate without a CSA-based treatment.

15. The method of claim 1, wherein the tissue-specific stem cells comprise one or more of follicular stem cells, hematopoietic stem cells, neural stem cells, epithelial stem cells of the gut, or tissue stem cells found in peripheral blood, brain, spinal cord, dental pulp, blood vessels, skeletal muscle, cornea, retina, liver, or pancreas.

16. The method of claim 1, wherein the treatment is administered without separately collecting, mixing, or culturing stem cells.

17. A method of stimulating hair growth and/or preventing hair loss, the method comprising:
providing a treatment composition including one or more cationic steroidal antimicrobial (CSA) compounds in a carrier;
applying the treatment composition to a dermal region of a subject in need of stimulating hair growth and/or preventing hair loss, wherein the subject is a human and the dermal region is the scalp; and
the one or more CSA compounds regenerating hair follicles and stimulating hair growth and/or preventing hair loss at the dermal region to which it is applied.

18. The method of claim 17, wherein the dermal region is affected by hair loss or is at risk of being affected by hair loss as a result of one or more of hereditary condition, hormonal imbalance, or injury.

19. A method of regenerating tissue and/or preventing tissue atrophy, the method comprising:
providing a treatment composition including one or more cationic steroidal antimicrobial (CSA) compounds in a carrier;
directly applying the treatment composition to targeted tissue of a subject that not infected with a microbial infection, wherein the targeted tissue is tissue damaged as a result of stroke, an autoimmune disease, a brain injury, or a cardiac injury or disorder; and
the one or more CSA compounds stimulating local stem cells to proliferate and promote tissue regeneration and/or prevent tissue atrophy at the targeted tissue to which it is applied, wherein the local stem cells comprise one or more of follicular stem cells, hematopoietic stem cells, neural stem cells, epithelial stem cells of the gut or skin, or tissue stem cells found in bone marrow, peripheral blood, brain, spinal cord, dental pulp, blood vessels, skeletal muscle, cornea, retina, liver, and pancreas.

20. A method of stimulating hair growth and/or preventing hair loss, the method comprising:
providing a treatment composition including one or more cationic steroidal antimicrobial (CSA) compounds in a carrier;
applying the treatment composition to a dermal region of a subject in need of stimulating hair growth and/or preventing hair loss, wherein the treatment composition is applied to a dermal region that is not infected with a microbial infection or associated with a dermal tissue wound; and
the one or more CSA compounds regenerating hair follicles and stimulating hair growth and/or preventing hair loss at the dermal region to which it is applied.

* * * * *